(12) United States Patent
Shue et al.

(10) Patent No.: US 7,204,813 B2
(45) Date of Patent: Apr. 17, 2007

(54) CANNULA RETRACTABLE MEDICAL COLLECTION DEVICE

(76) Inventors: Ming-Jeng Shue, No. 14, Lane 8, Chung-I Street, Hsi District, Taichung City (TW); Deborah Huang, 7F, No. 5, Section 3, Liu-Chun E. Street, Chung District, Taichung City (TW); Phillip Shue, No. 14, Lane 8, Chung-I Street, Hsi District, Taichung City (TW)

( * ) Notice: Subject to any disclaimer, the term of this patent is extended or adjusted under 35 U.S.C. 154(b) by 304 days.

(21) Appl. No.: 10/775,738

(22) Filed: Feb. 9, 2004

(65) Prior Publication Data

US 2005/0101881 A1  May 12, 2005

(30) Foreign Application Priority Data

Nov. 7, 2003  (TW) .............................. 92131220 A

(51) Int. Cl.
*A61B 5/00*    (2006.01)
(52) U.S. Cl. .................................. 600/577
(58) Field of Classification Search ............... 600/576, 600/577; 604/110, 187
See application file for complete search history.

(56) References Cited

U.S. PATENT DOCUMENTS

| | | | |
|---|---|---|---|
| 4,892,107 A | | 1/1990 | Haber |
| 4,947,863 A | * | 8/1990 | Haber et al. ................. 600/577 |
| 5,030,209 A | | 7/1991 | Wanderer et al. |
| 5,070,885 A | * | 12/1991 | Bonaldo ....................... 600/576 |
| 5,219,333 A | * | 6/1993 | Sagstetter et al. ........... 604/110 |
| 5,562,103 A | | 10/1996 | Sak |
| 5,709,669 A | | 1/1998 | Haining |
| 2002/0123721 A1 | | 9/2002 | Payne et al. |

FOREIGN PATENT DOCUMENTS

| | | |
|---|---|---|
| EP | 0329038 A1 | 8/1989 |
| WO | WO 89/04141 A1 | 5/1989 |
| WO | WO 90/02515 A1 | 3/1990 |
| WO | WO 92/20281 A1 | 11/1992 |

* cited by examiner

*Primary Examiner*—Max Hindenburg
*Assistant Examiner*—Fangemonique Smith
(74) *Attorney, Agent, or Firm*—Townsend and Townsend and Crew LLP

(57) ABSTRACT

A cannula retractable medical collection device includes a cannula mount inserted into and axially slidable relative to a rear larger-diameter wall portion of a barrel, a double-ended needle cannula including a rear needle segment extending into an accommodation chamber in the cannula mount for pricking a stopper of a collection vial, and a front needle segment secured to the cannula mount by a needle hub. The front needle segment extends outwardly of the barrel in a position of use, and retreats inwardly and rearwardly of the barrel in a disposal position when the cannula mount is in the front and rear positions, respectively. A releasably retaining member includes a retaining hole formed in the larger-diameter wall portion, and a radially extending engaging peg engageable in the hole. An actuator is operable to disengage the peg from the hole so as to permit axial movement of the cannula mount.

16 Claims, 21 Drawing Sheets

CANNULA RETRACTABLE MEDICAL COLLECTION DEVICE

CROSS-REFERENCE TO RELATED APPLICATION

This application claims priority of Taiwanese Application No. 092131220, filed on Nov. 7, 2003.

BACKGROUND OF THE INVENTION

1. Field of the Invention

This invention relates to a cannula retractable medical collection device, more particularly to a cannula retractable medical collection device adapted to be used with a collection vial for collecting a blood sample therein, and having a cannula which is retractable into a barrel for safe disposal.

2. Description of the Related Art

Referring to FIGS. 1 and 2, U.S. Pat. No. 5,810,775 discloses a cap operated retractable medical device 1, which includes an outer body 11 with a hingedly connected outer cap 16 that is movable between open and closed positions. A movable member 12 is entirely mounted within the outer body 11. A retracting body 13 is held in a front end 121 of the movable member 12 by means of friction interference therebetween such that the front end 121 is frictionally fitted with the outer body 11 adjacent to a stop 112 formed on the outer body 11. A double-ended needle cannula 14 is installed in the retracting body 13. A biasing spring 15 is compressed between the retracting body 13 and the stop 112.

In use, a front needle end 142 of the needle cannula 14 is inserted into a patient's vein. A conventional rubber stopper collection vial (not shown) is inserted into the outer body 11 from an open back 111 thereof, and is pushed forward such that a rear needle end 141 of the needle cannula 14 punctures the rubber stopper and passes through a rubber sheath 17 for collecting a blood sample in the collection vial. The collection vial is then removed from the device 1 while the sheath 17 can restrict further flow of the blood. Thereafter, the cap 16 is operated to the closed position to engage an open back end 122 of the movable member 12 so as to move the movable member 12 forward, thereby triggering retraction of the retracting body 13 and the needle cannula 14.

Although the needle canula 14 can be retracted after use, the following drawbacks arise:

1. Since the collection vial has an outer diameter smaller than that of the movable member 12, a clearance exists therebetween so that the collection vial tends to shake during use, thereby resulting in pain to the patient.

2. Before retraction of the needle cannula 14, such as during transportation, before and during blood collection, the cap 16 has to be kept in the open position to prevent undesired retraction of the needle cannula 14, thereby resulting in inconvenient storage and transportation of the device 1.

3. The blood in the needle cannula 14 is not visible, thereby causing inconvenience to the user.

Furthermore, intravenous catheter inserting devices are generally used to administer medication fluid into or to draw blood from a patient's vein. Referring to FIG. 3, a conventional intravenous catheter inserting device 9 is shown to include a tubular needle seat 91 with a hub end 911, a needle cannula 92 secured to the hub end 911, a catheter hub 93 sleeved on the needle seat 91, and a flexible tubular catheter 94 secured to the catheter hub 93. In use, the catheter 94 and the needle cannula 92 are inserted into the patient's vein by a health care worker by piercing the patient's vein with a sharp tip of the needle cannula 92 which projects outwardly of the catheter 94. The health care worker then withdraws the needle cannula 92 from the catheter 94 with one hand and, at the same time, applies pressure to the patient's skin with the other hand, thereby leaving the catheter 94 in the patient's vein. Subsequently, a transfusion member (not shown) with medication fluid or an empty barrel is connected to the catheter hub 93 for administering the medication fluid into the patient's vein or for drawing blood. At this time, as the health care worker must place the used needle cannula 92 and the needle seat 91 on a tray (not shown) nearby, the exposed sharp tip of the used needle cannula 92 may create a danger of an accidental needle stick. Moreover, blood contamination may occur during connection of the catheter hub 93 to the transfusion member or the empty barrel.

SUMMARY OF THE INVENTION

An object of the present invention is to provide a canula retractable medical collection device which can be operated easily to retract a used needle canula with one hand.

Another object of the present invention is to provide a cannula retractable medical collection device which can be used with an intravenous catheter device for performing an intravenous injection.

According to this invention, the cannula retractable medical collection device includes a barrel having front and rear open ends opposite to each other in a longitudinal direction, and a surrounding barrel wall interconnecting and interposed therebetween. The surrounding barrel wall includes a front smaller-diameter wall portion and a rear larger-diameter wall portion which are opposite to each other in the longitudinal direction and which are proximate to the front and rear open ends, respectively. The surrounding barrel wall has an inner barrel wall surface which surrounds an axis in the longitudinal direction and which confines a passage communicated with the front and rear open ends, and an outer barrel wall surface opposite to the inner barrel wall surface in radial directions relative to the axis.

A cannula mount is inserted into the passage from the rear open end, and is slidable relative to the rear larger-diameter wall portion along the axis between front and rear positions to be proximate to the smaller-diameter wall portion and the rear open end, respectively. The cannula mount includes a shell member which has a skirt portion surrounding the axis and confining an accommodation chamber therein for receiving a front vial end of a collection vial, and an interconnecting portion opposite to the skirt portion in the longitudinal direction. The interconnecting portion defines an axial passageway extending therethrough to be communicated with the accommodation chamber.

A needle cannula includes front and rear needle segments which are opposite to each other in the longitudinal direction, and which have front and rear needle taper points, respectively. The rear needle segment extends into the accommodation chamber through the axial passageway along the axis so as to enable the rear needle taper point to be adapted to prick a pierceable stopper on the front vial end of the collection vial.

A needle hub is disposed to secure the front needle segment to the interconnecting portion such that the front needle segment is in fluid communication with the rear needle segment, and such that when the cannula mount is in the front position, the front needle segment is placed in a position of use, where the front needle segment extends outwardly of the front open end for ready use, and when the cannula mount is in the rear position, the front needle segment is placed in a disposal position, where the front needle segment retreats inwardly and rearwardly of the front open end.

A releasably retaining member is disposed to arrest axial movement of the cannula mount relative to the barrel when the cannula mount is in the front position, and includes a retaining hole and an engaging peg. The retaining hole is formed in the outer barrel wall surface of the larger-diameter wall portion, and extends in a radial direction through the inner barrel wall surface. The engaging peg extends in the radial direction, and is engageable in the retaining hole to establish an interengagement between the larger-diameter wall portion and the skirt portion such that movement of the cannula mount at the front position is arrested.

An actuator is operable externally, and is disposed to enable the engaging peg to be disengaged from the retaining hole to permit the axial movement of the cannula mount to the rear position.

BRIEF DESCRIPTION OF THE DRAWINGS

Other features and advantages of the present invention will become apparent in the following detailed description of the preferred embodiments of the invention, with reference to the accompanying drawings, in which.

DETAILED DESCRIPTION OF THE PREFERRED EMBODIMENTS

Figure 1:
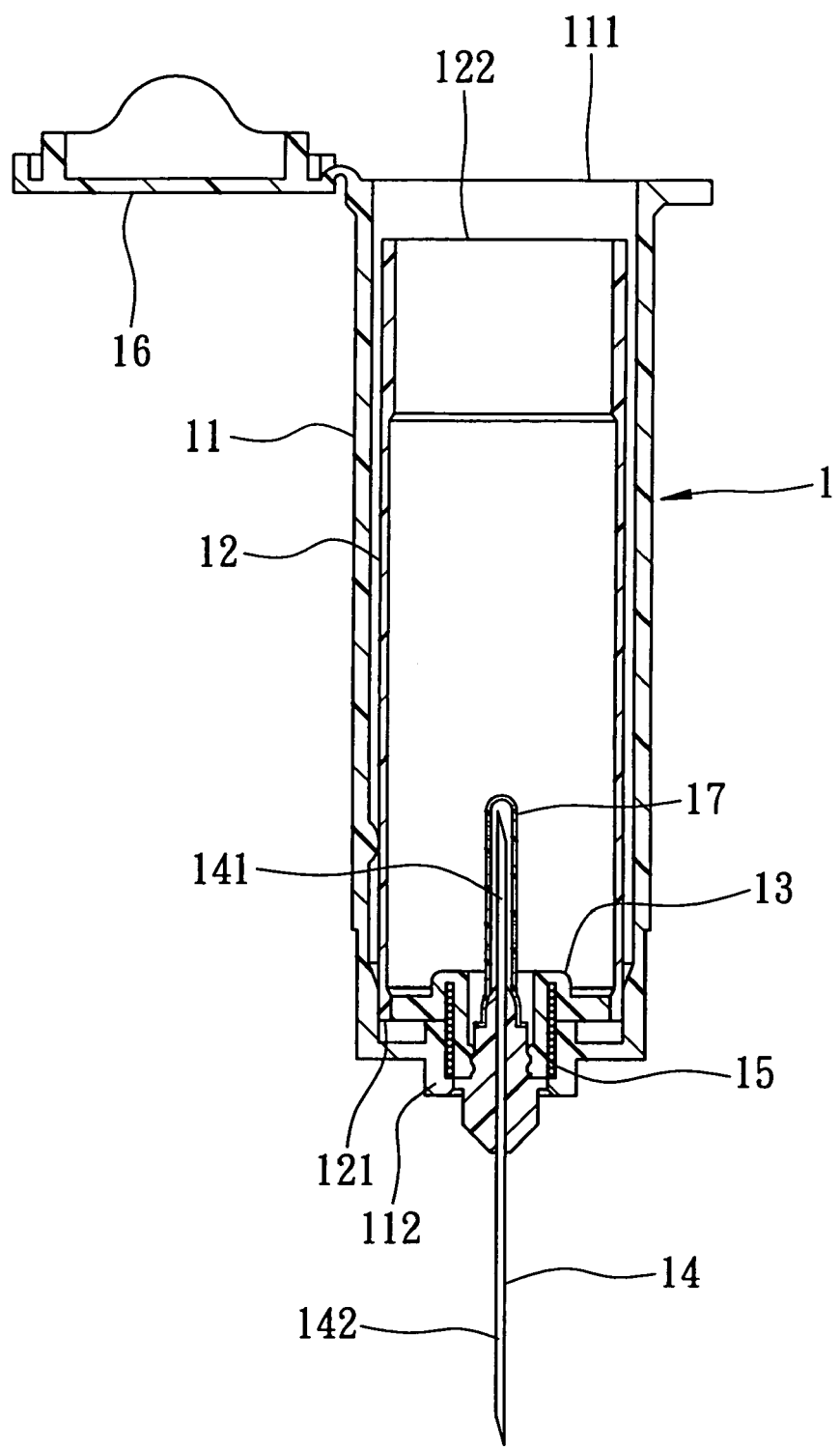
FIG. 1 is a sectional view of a conventional medical device in a ready-to-use position.
Figure 2:
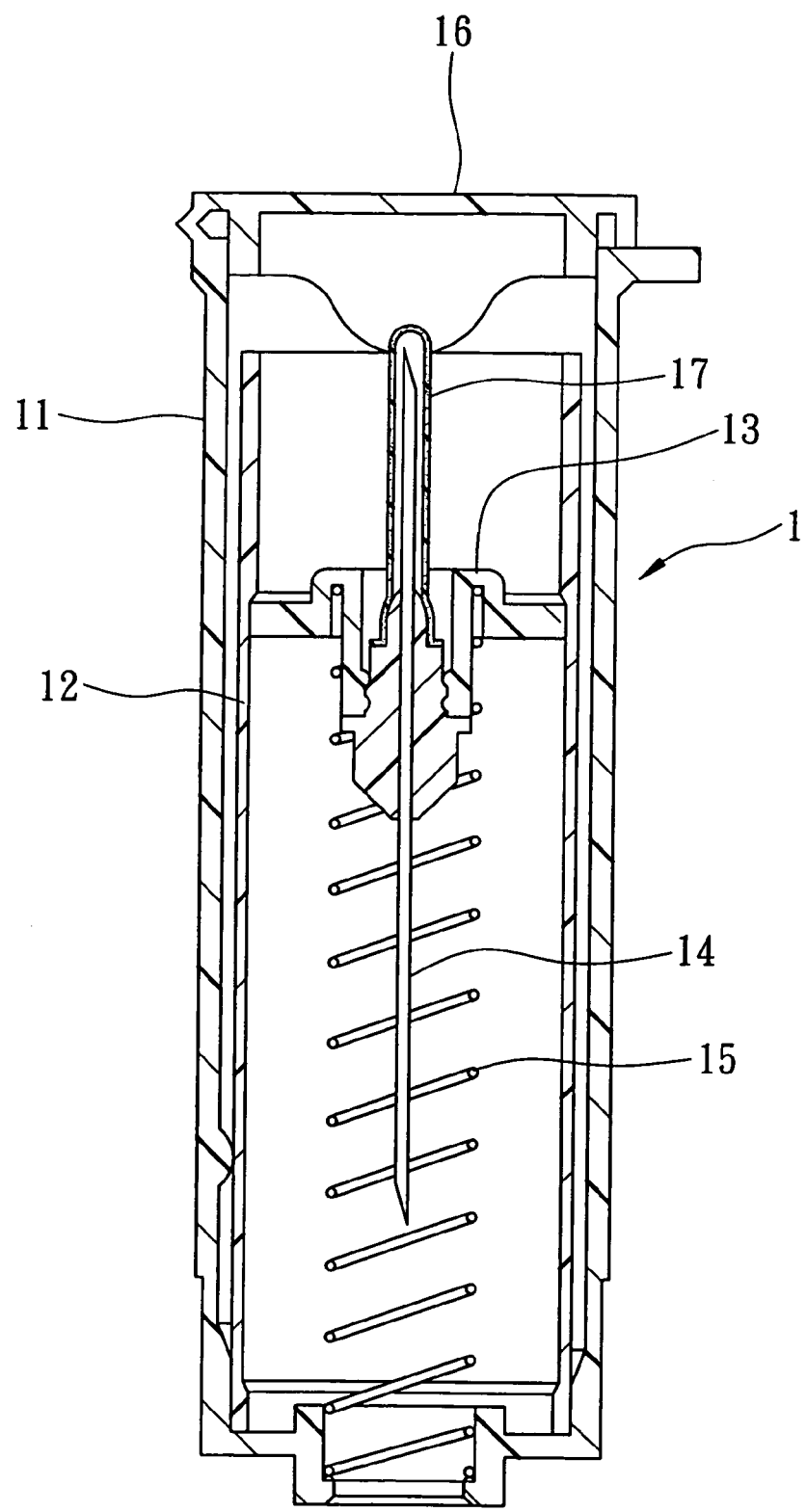
FIG. 2 is a sectional view of the conventional medical device after a cap thereof has been moved from an opened position to a closed position.
Figure 3:
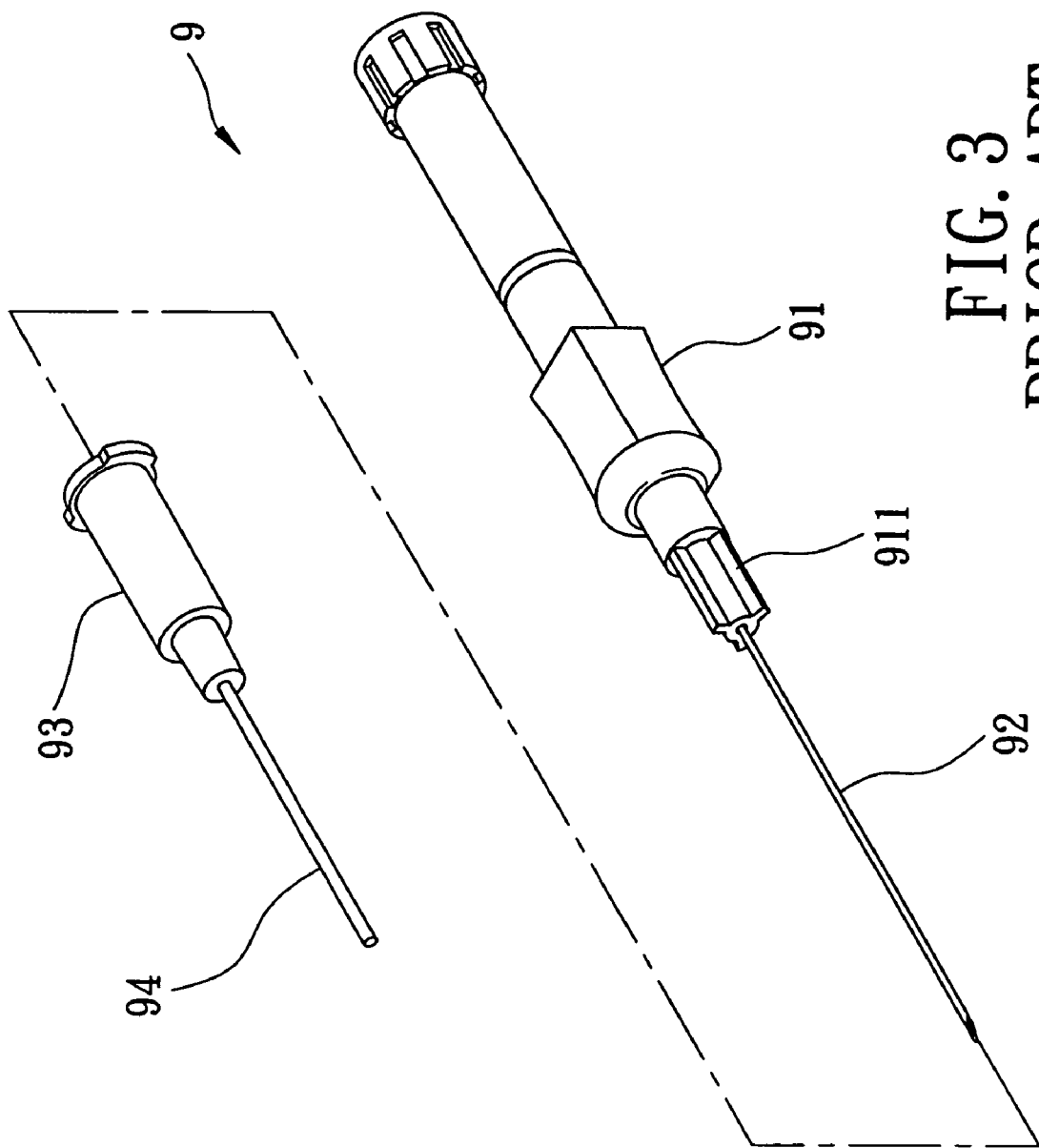
FIG. 3 is an exploded perspective view of a conventional intravenous catheter inserting device.

Before the present invention is described in greater detail, it should be noted that same reference numerals have been used to denote like elements throughout the specification.

Figure 4:
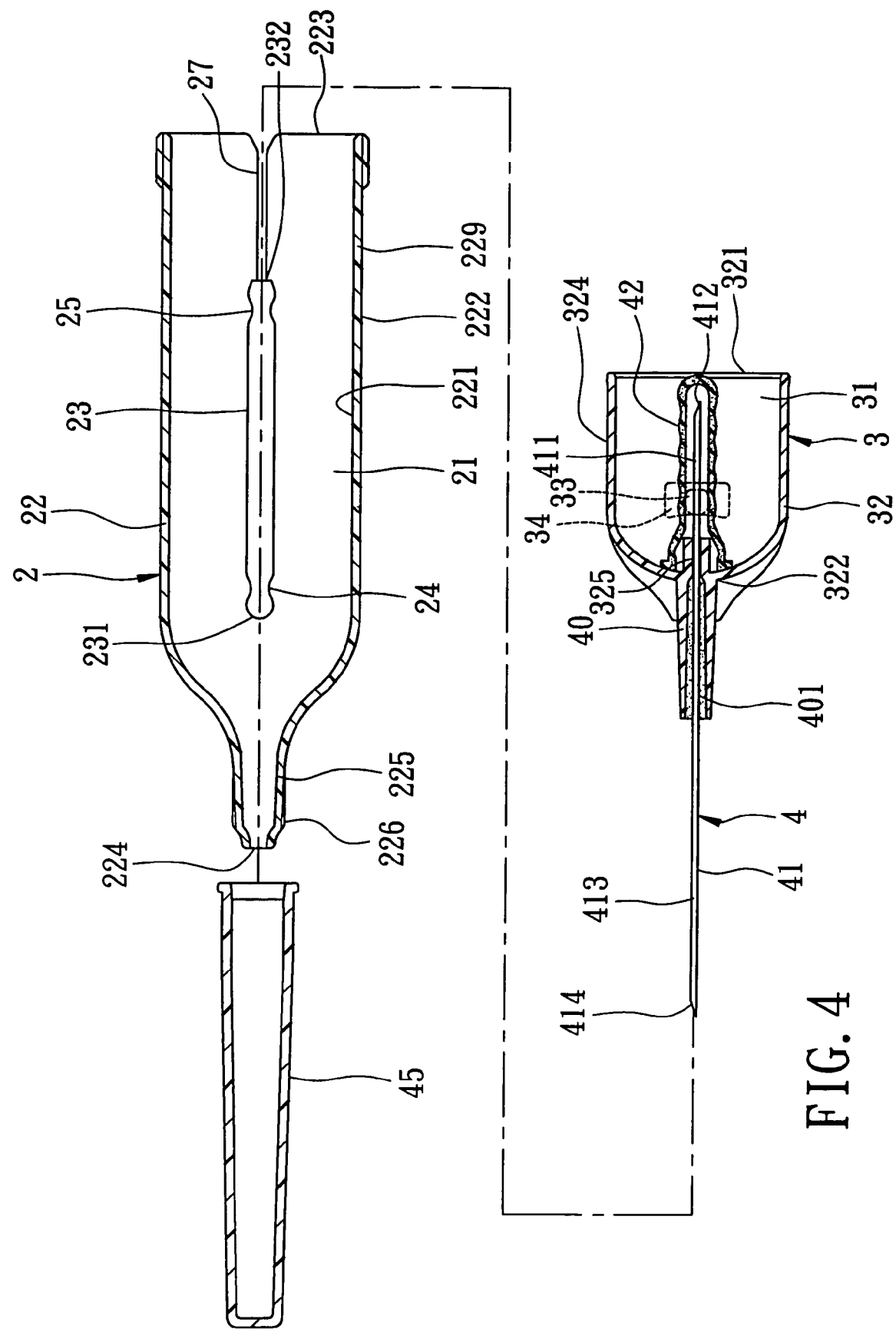
FIG. 4 is an exploded sectional view of the first preferred embodiment of a cannula retractable medical collection device according to this invention.
Figure 5:
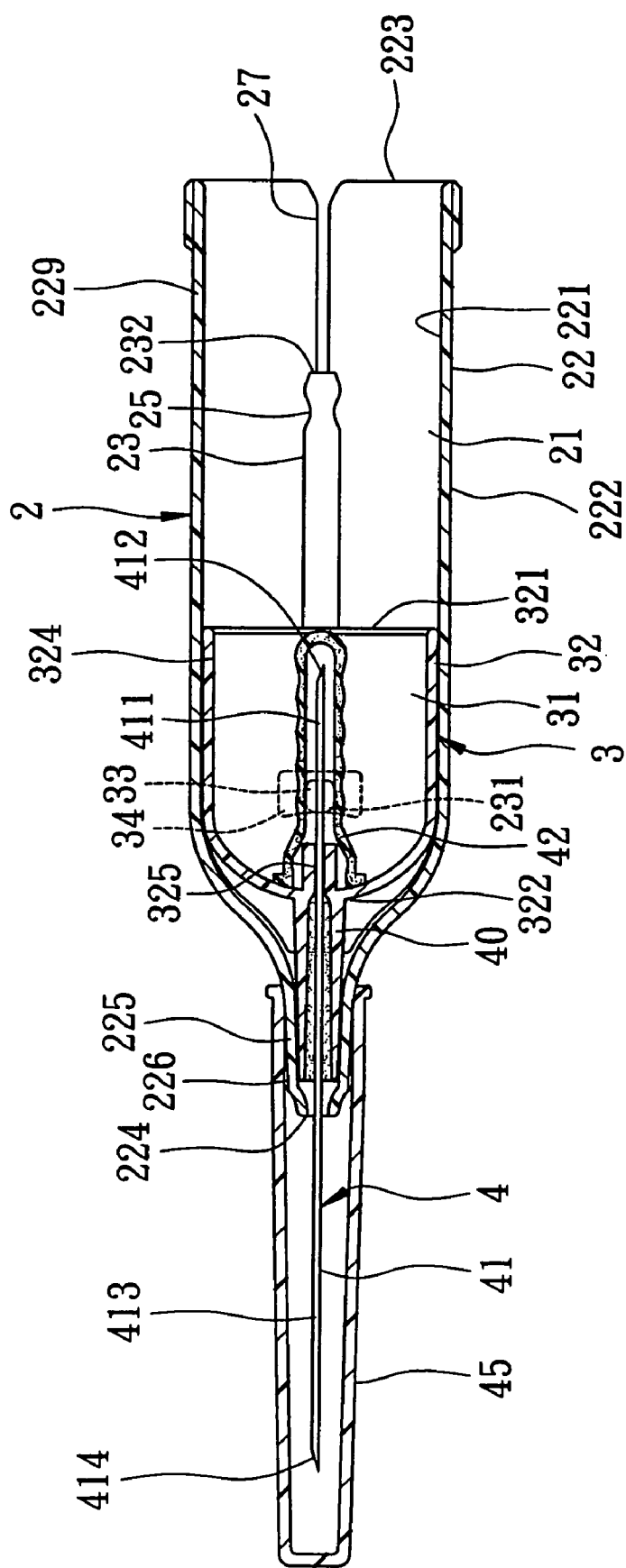
FIG. 5 is a sectional view of the first preferred embodiment in a ready-to-use state.
Figure 6:
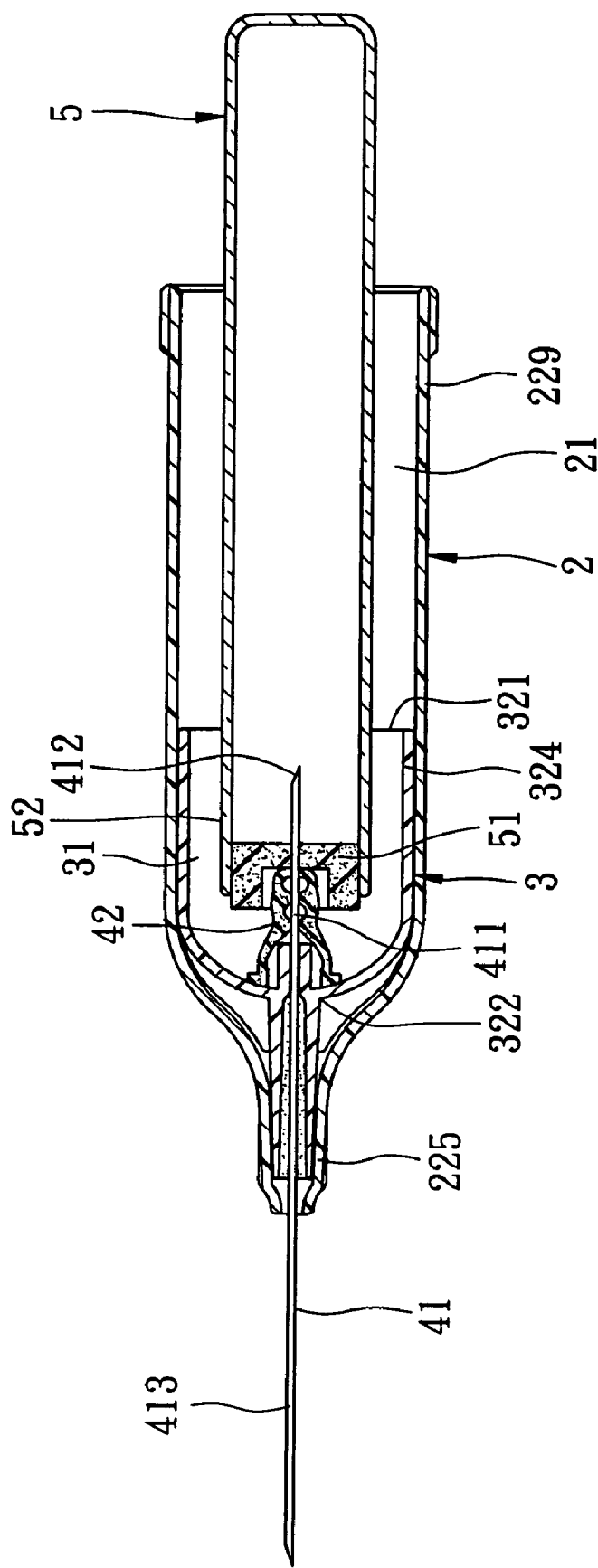
FIG. 6 is a sectional view of the first preferred embodiment in a state where a collection vial is received in a barrel during use.

Referring to FIGS. 4 to 6, the first preferred embodiment of a cannula retractable medical collection device according to the present invention is shown to comprise a barrel 2, a cannula mount 3, and a needle assembly 4.

The barrel 2 has front and rear open ends 224,223 opposite to each other in a longitudinal direction, and a surrounding barrel wall 22 which interconnects and which is interposed between the front and rear open ends 224,223. The surrounding barrel wall 22 includes a front smaller-diameter wall portion 225 and a rear larger-diameter wall portion 229 which are opposite to each other in the longitudinal direction and which are proximate to the front and rear open ends 224,223, respectively. The surrounding barrel wall 22 has an inner barrel wall surface 221 which surrounds an axis in the longitudinal direction and which confines a passage 21 communicated with the front and rear open ends 224,223, and an outer barrel wall surface 222 opposite to the inner barrel wall surface 221 in radial directions relative to the axis.

A releasably retaining member includes a retaining hole 231 which is formed in the outer barrel wall surface 222 of the larger-diameter wall portion 229, and which extends in a radial direction through the inner barrel wall surface 221. The larger-diameter wall portion 229 has an elongated guideway 23 which extends from the outer barrel wall surface 222 through the inner barrel wall surface 221 in the radial direction, and which is elongated from the retaining hole 231 rearwardly and in the longitudinal direction to terminate at a rear retaining end 232. The elongated guideway 23 has front and rear constricted regions 24,25 which are formed immediately behind the retaining hole 231 and immediately in front of the rear retaining end 232, respectively.

The cannula mount 3 is inserted into the passage 21 from the rear open end 223, and is slidable relative to the rear larger-diameter wall portion 229 along the axis between front and rear positions to be proximate to the smaller-diameter wall portion 225 and the rear open end 223, respectively. The cannula mount 3 includes a shell member 32 which has a skirt portion 324 and an interconnecting portion 322 opposite to the skirt portion 324 in the longitudinal direction. The skirt portion 324 surrounds the axis and confines an accommodation chamber 31 therein with a rear insert end 321 such that a front vial end 52 of a collection vial 5 is inserted into the accommodation chamber 31 from the rear insert end 321. The interconnecting portion 322 defines an axial passageway 325 which extends therethrough into and to communicate with the accommodation chamber 31.

The releasably retaining member further includes an engaging peg 33 disposed on and extending in the radial direction from the skirt portion 324 to terminate at a shifted end which extends radially and outwardly of the outer barrel wall surface 222. The engaging peg 33 is slidable along the elongated guideway 23 from the retaining hole 231 to the rear retaining end 232 when the cannula mount 3 slides from the front position to the rear position. Thus, the engaging peg 33 is engageable in the retaining hole 231 or the rear retaining end 232 to form an interengagement between the larger-diameter wall portion 229 and the skirt portion 324. When the cannula mount 3 is disposed at the front or rear position, axial movement of the cannula mount 3 relative to the barrel 2 is arrested by a corresponding one of the front and rear constricted regions 24,25. Once the engaging peg 33 is forced through one of the front and rear constricted regions 24,25, movement of the engaging peg 33 is arrested by virtue of a snap-fit in a corresponding one of the retaining hole 231 and the rear retaining end 232 so as to position the cannula mount 3 in a corresponding one of the front and rear positions. Preferably, the larger-diameter wall portion 229 further has a split 27 which extends from the rear retaining end 232 to the rear open end 223 so as to vest the elongated guideway 23 with an increased flexibility along the radial direction, thereby facilitating the forced movement of the engaging peg 33 through the front and rear constricted regions 24,25, and facilitating the assembly of the engaging peg 33 into the elongate guideway 23 through the split 27.

An enlarged actuator 34 is formed integrally with the shifted end of the engaging peg 33, and is disposed outwardly of and is slidable relative to the outer barrel wall surface 222 so as to be operable externally to enable the engaging peg 33 to be disengaged from the retaining hole 231, thereby permitting the axial movement of the cannula mount 3 to the rear position along the elongated guideway 23.

The needle assembly 4 includes a needle hub 40, a double-ended needle cannula 41, a rubber sheath 42, and a tip protector 45.

The needle hub 40 is formed integrally with the cannula mount 3, and is confined in the smaller-diameter wall portion 225 where the inner barrel wall surface 221 converges gradually from the larger-diameter wall portion 229 towards the front open end 224 so as to prevent removal of the needle hub 40 from the front open end 224 and to facilitate approaching of the medical collecting device to skin and subcutaneous vessels. The needle hub 40 has a cannula holding passage 401 extending therethrough along the axis and fluidly communicated with the axial passageway 325 in the interconnecting portion 322 of the cannula mount 3.

The double-ended needle cannula 41 passes through the cannula holding passage 401, and includes front and rear needle segments 413,411 which are integrally formed with each other, which are opposite to each other in the longitudinal direction, and which have front and rear needle taper points 414,412, respectively. The rear needle segment 411 extends into the accommodation chamber 31 through the axial passageway 325 along the axis. The rubber sheath 42 sealingly engages the interconnecting portion 322 and covers the rear needle segment 411. The tip protector 45 is sleeved on the outer barrel wall surface 222 of the smaller-diameter wall portion 225, and is frictionally fitted to a rib portion 226 on the smaller-diameter wall portion 225 so as to ensure shielding of the front needle segment 413.

In use, the collection device of this embodiment is disposed in a state shown in FIG. 5, where the front needle segment 413 is placed in a position of use and extends outwardly of the front open end 224 for ready use, and where the engaging peg 33 is retained in the retaining hole 231 to arrest the cannula mount 3 at the front position. After the tip protector 45 is removed, the front needle taper point 414 is inserted into a patient's vein so as to permit blood to flow into the rubber sheath 42. Referring to FIG. 6, the collection vial 5 is then inserted into the accommodation chamber 31, and is pushed forward to enable the rear needle taper point 412 to prick a pierceable stopper 51 covering the front vial end 52 of the collection vial 5 and to pass through the rubber sheath 42, thereby permitting collection of a blood sample in the collection vial 5.

Figure 7:
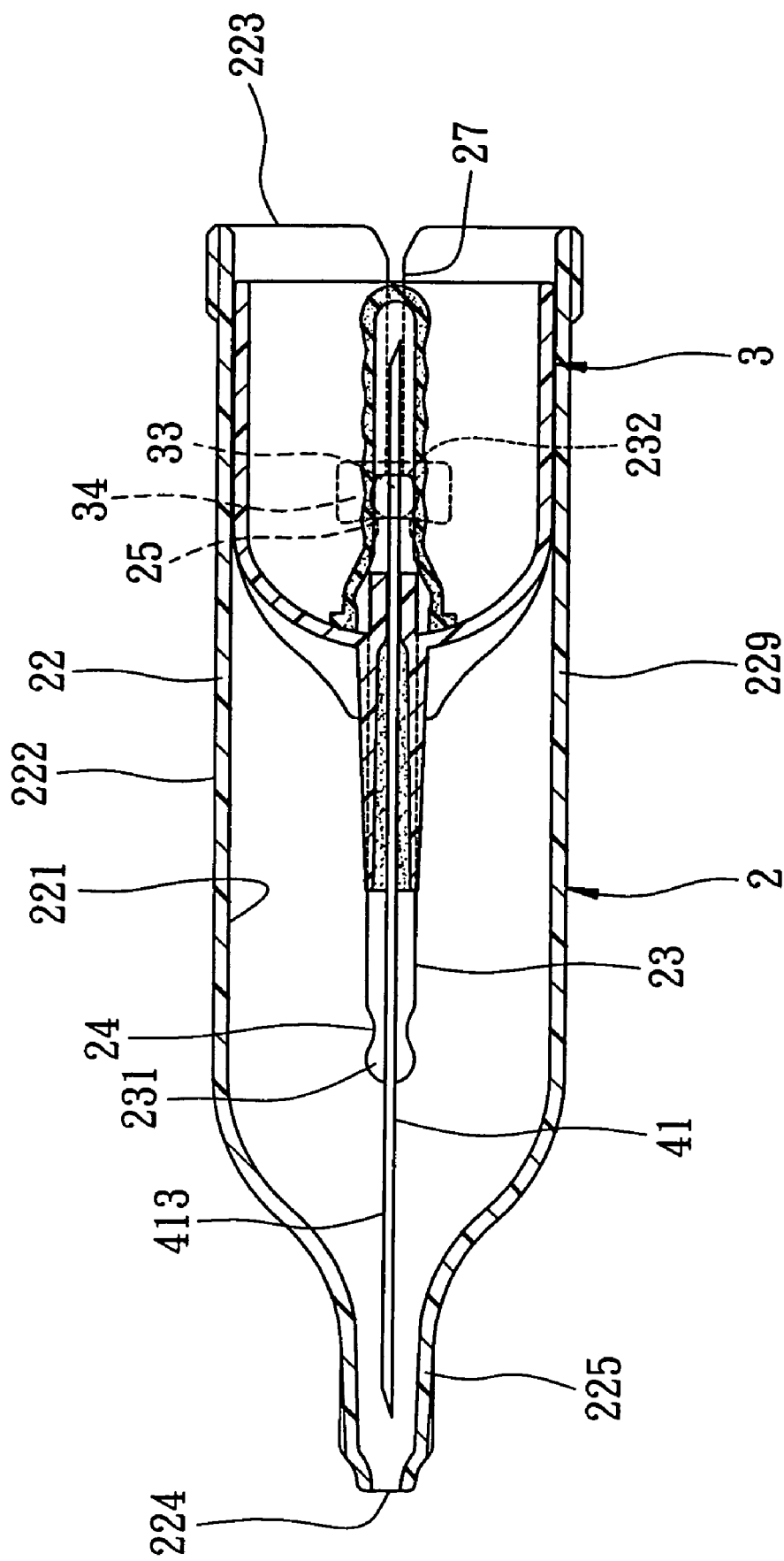
FIG. 7 is a sectional view of the first preferred embodiment in a state where a needle cannula is retracted into the barrel.

When the collection vial 5 is removed from the collection device after completion of blood collection, the actuator 34 is operated with the finger of the hand holding the collection device to move the engaging peg 33 rearward along the elongated guideway 23 to thereby bring the cannula mount 3 to the rear position, as shown in FIG. 7, such that the front needle segment 413 is placed in a disposal position to retreat inwardly and rearwardly of the front open end 224 for safe disposal.

Figure 8:
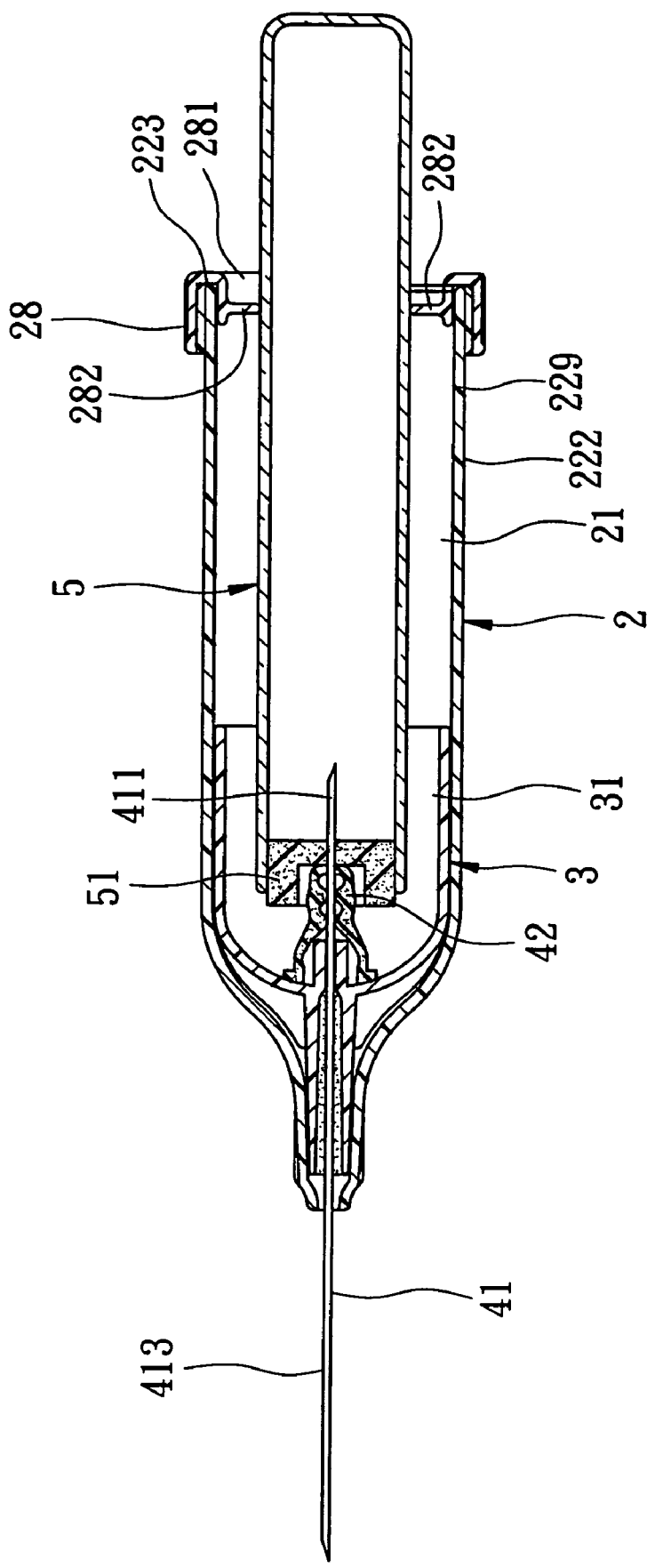
FIG. 8 is a sectional view of the first preferred embodiment wherein an end cap is further provided on the barrel.
Figure 9:
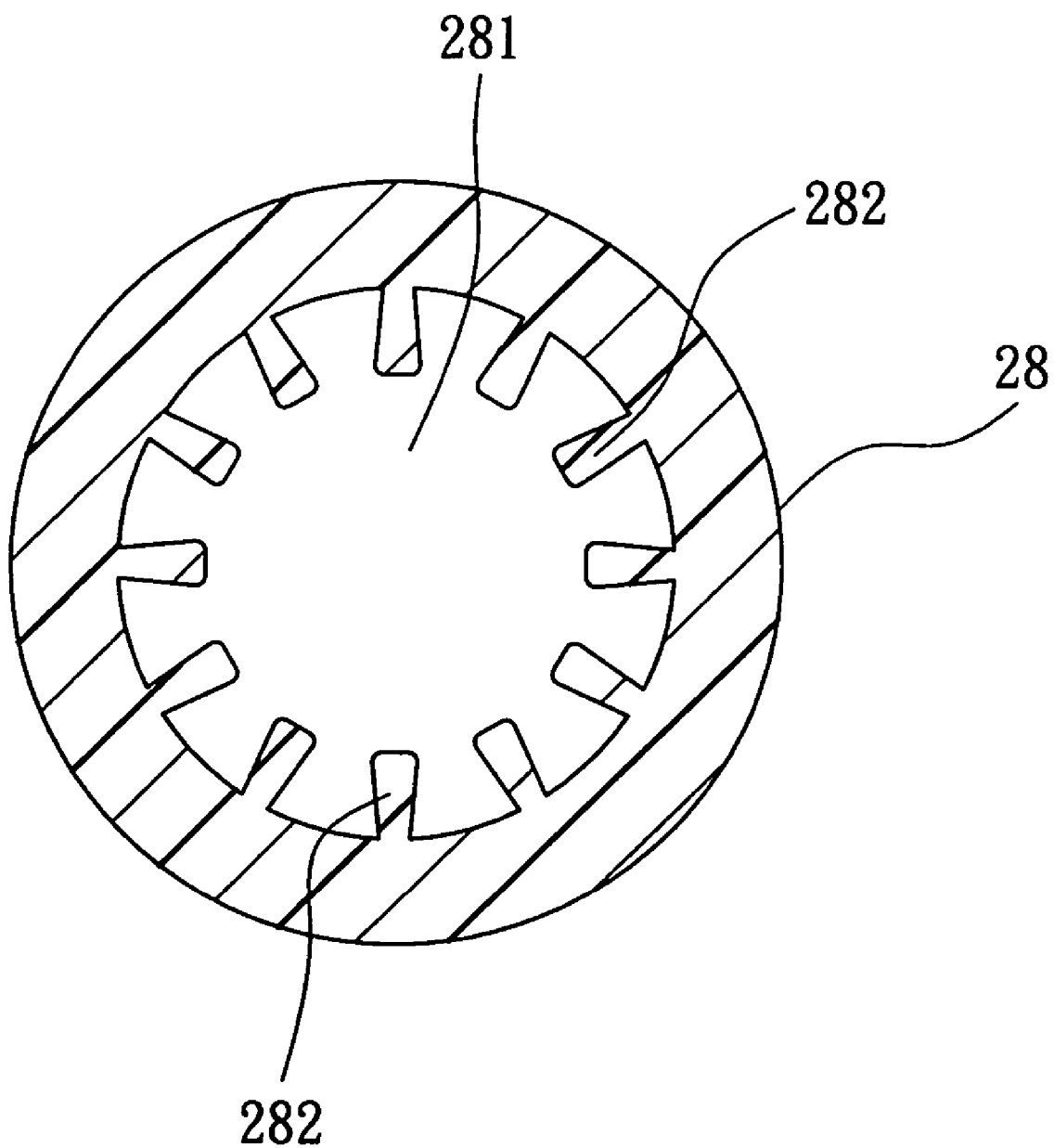
FIG. 9 is a cross-sectional view of the end cap shown in FIG. 8.

Referring to FIGS. 8 and 9, preferably, an end cap 28 is mounted on the outer barrel wall surface 222 of the larger-diameter wall portion 229 adjacent to the rear open end 223. The end cap 28 has an opening 281 formed therethrough along the axis, and a plurality of deformable protrusions 282 which extend radially and inwardly into the opening 281 and which are angularly displaced from one another so as to be adapted to hold the collection vial 5 by frictional engagement therewith along the axis. Thus, the collection vial 5 can be inserted into the collection device and can be retained by the deformable protrusions 282 before the needle cannula 41 is inserted into the patient's vein, thereby resulting in convenient operation of the collection device.

Figure 10:
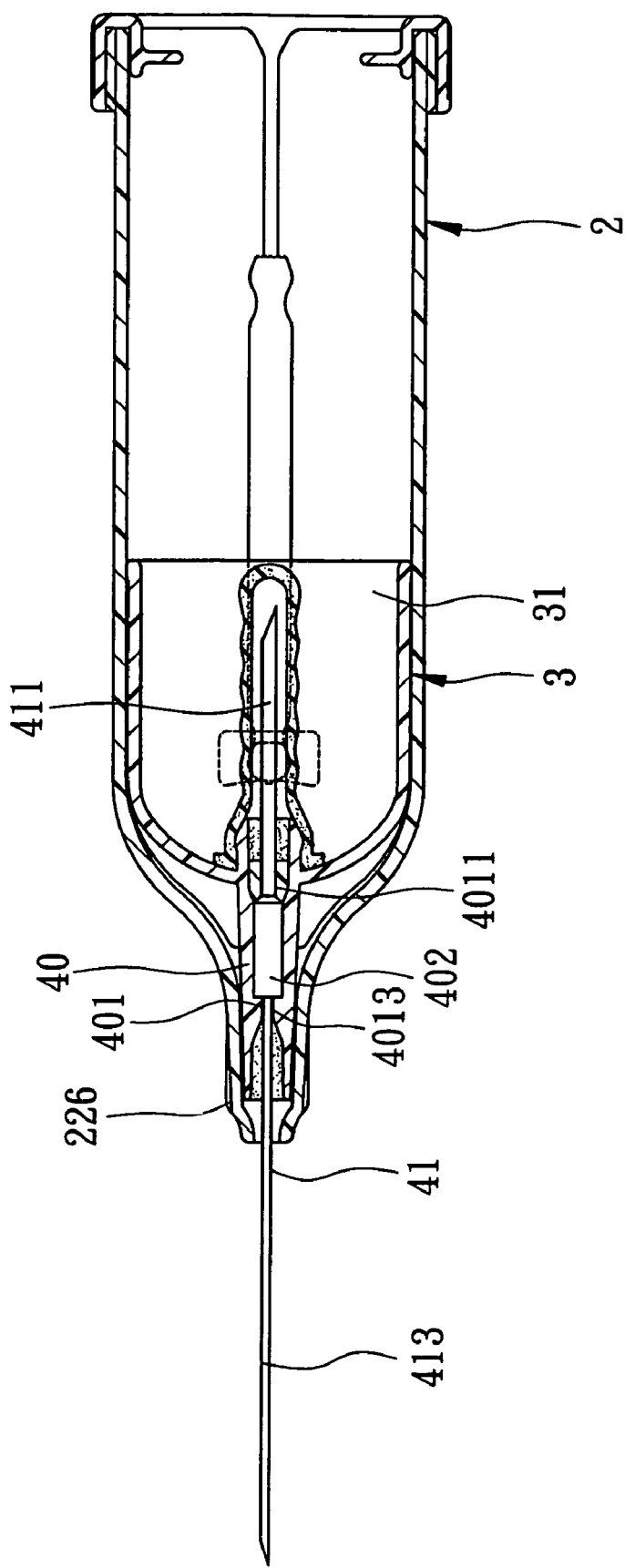
FIG. 10 is a sectional view of the second preferred embodiment of a cannula retractable medical collection device according to this invention.

Referring to FIG. 10, the second preferred embodiment of a cannula retractable medical collection device of this invention is shown to be similar to the previous embodiment in construction, except that the needle hub 40 has a cannula holding passage 401 which includes front and rear passage segments 4013,4011 that respectively receive the front and rear needle segments 413,411 of the needle cannula 41 configured as two separate parts, and an enlarged intermediate portion 402 that interconnects the front and rear passage segments 4013,4011 and that is light transmissible to permit viewing of blood flowing therethrough so as to enable the user to check whether the needle cannula 41 has been inserted properly into the patient's vein.

Figure 11:
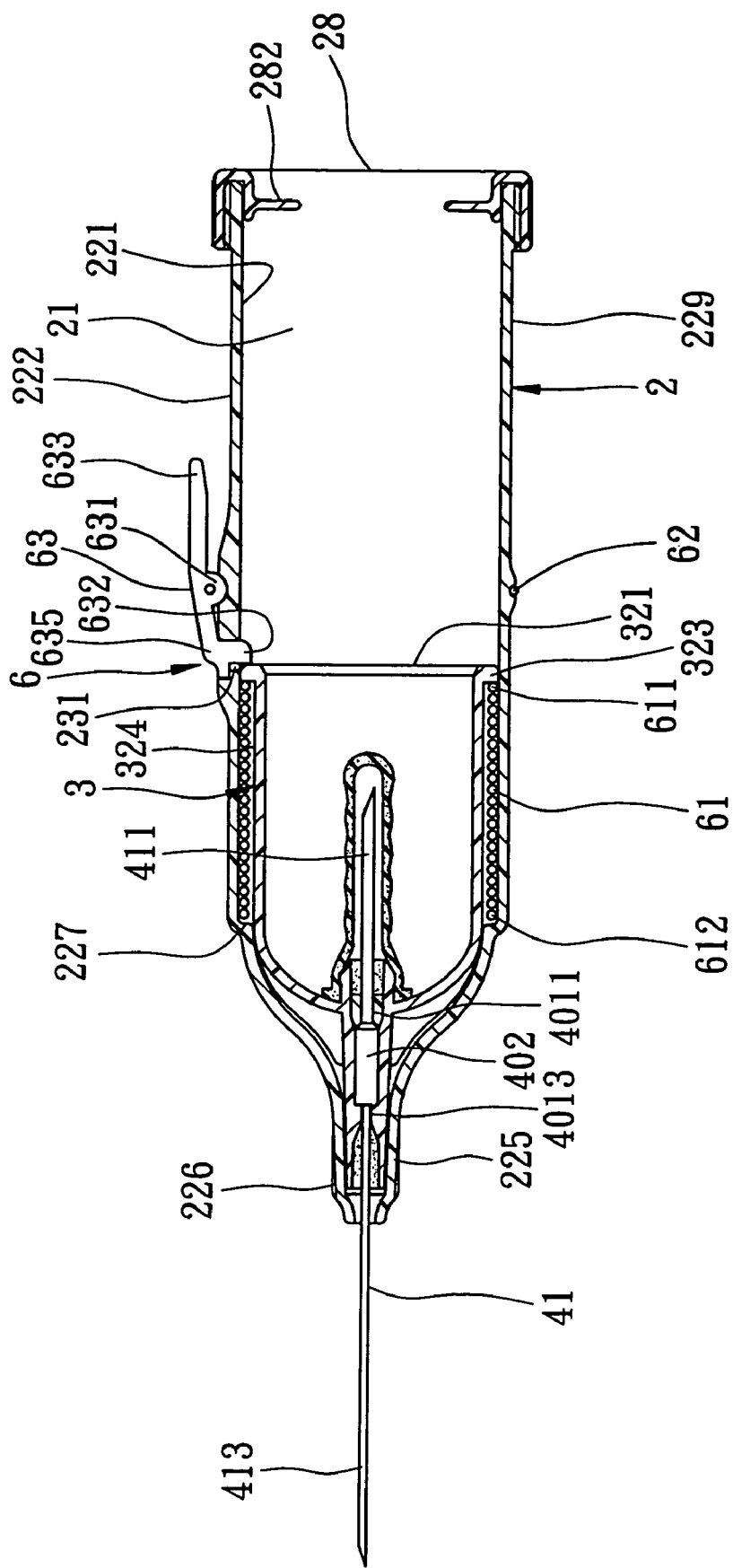
FIG. 11 is a sectional view of the third preferred embodiment of a cannula retractable medical collection device according to this invention.
Figure 12:
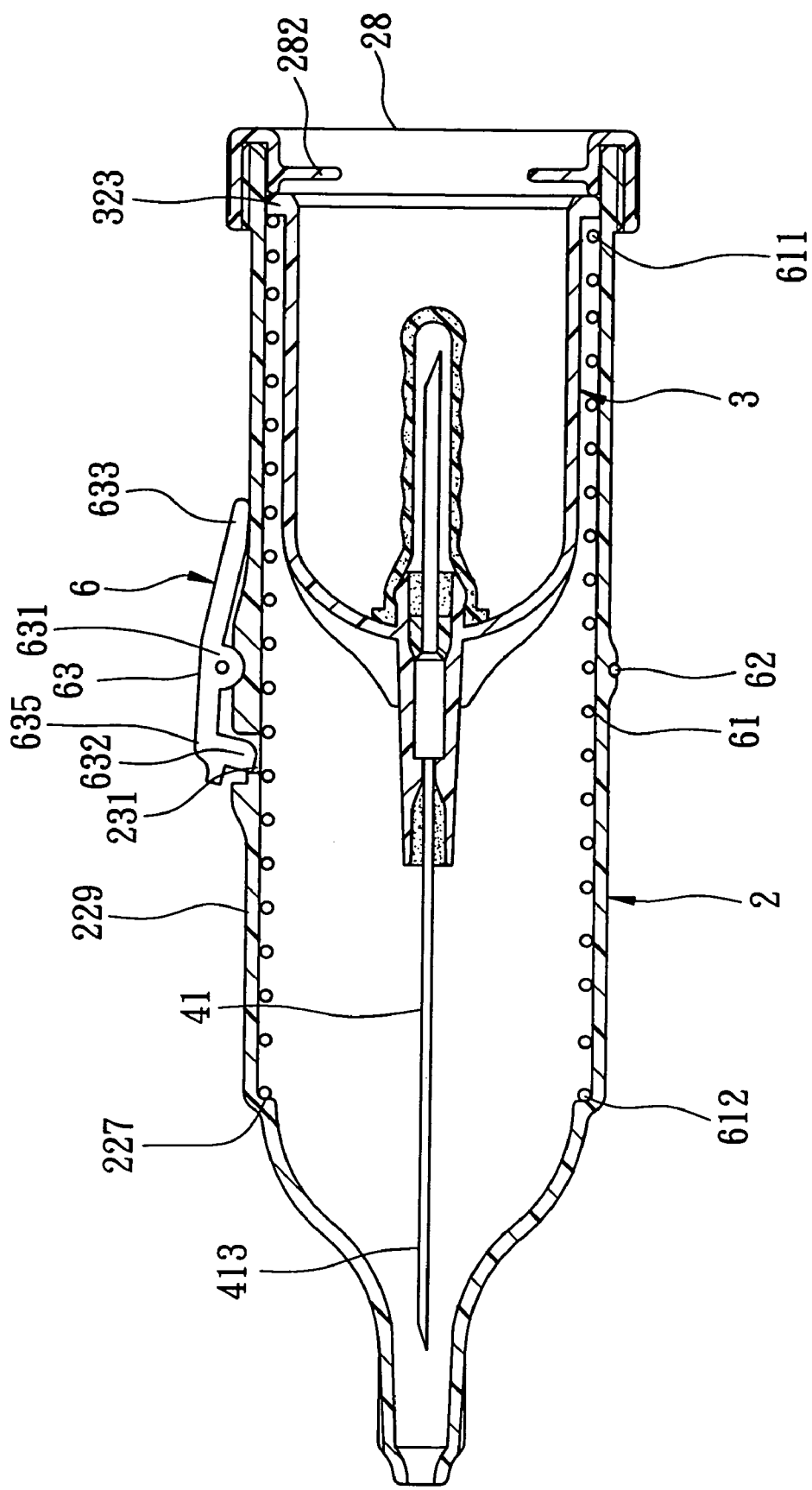
FIG. 12 is a sectional view of the third preferred embodiment, showing a needle cannula in a retracted state.

Referring to FIGS. 11 and 12, the third preferred embodiment of a cannula retractable medical collection device of this invention is shown to be similar to the second preferred embodiment in construction. The differences reside in that the actuator 6 includes a triggering member 63 formed as a lever which is mounted pivotally on the outer barrel wall surface 222 at a fulcrum point 631 by means of a C-shaped clip 62 that is sleeved on the outer barrel wall surface 222. The triggering member 63 includes a weight end 635 formed integrally with the engaging peg 632, and a power end 633 disposed at an opposite side of the weight end 635 relative to the fulcrum point 631 so as to be actuated to move the engaging peg 632 in the radial direction to withdraw from the passage 21 to thereby release the cannula mount 3.

Furthermore, the inner barrel wall surface 221 of the larger-diameter wall portion 229 has an annular shoulder 227 formed adjacent to the smaller-diameter wall portion 225. The skirt portion 324 of the cannula mount 3 has an annular flange 323 disposed at the rear insert end 321 and confronting the annular shoulder 227 in the longitudinal direction so as to define a biasing member receiving space therebetween and outside of the skirt portion 324. A biasing member, such as a coiled spring 61, is received in the biasing member receiving space, and includes front and rear spring ends 612,611 abutting against the shoulder 227 and the flange 323, respectively, such that the coiled spring 61 is compressed by the cannula mount 3 when the cannula mount 3 is in the front position. Due to the provision of the coiled spring 61, when the power end 633 is depressed with the finger to retract the engaging peg 632 radially, the cannula mount 3 is moved to the rear position so as to bring the needle cannula 41 to the disposal position.

Figure 13:
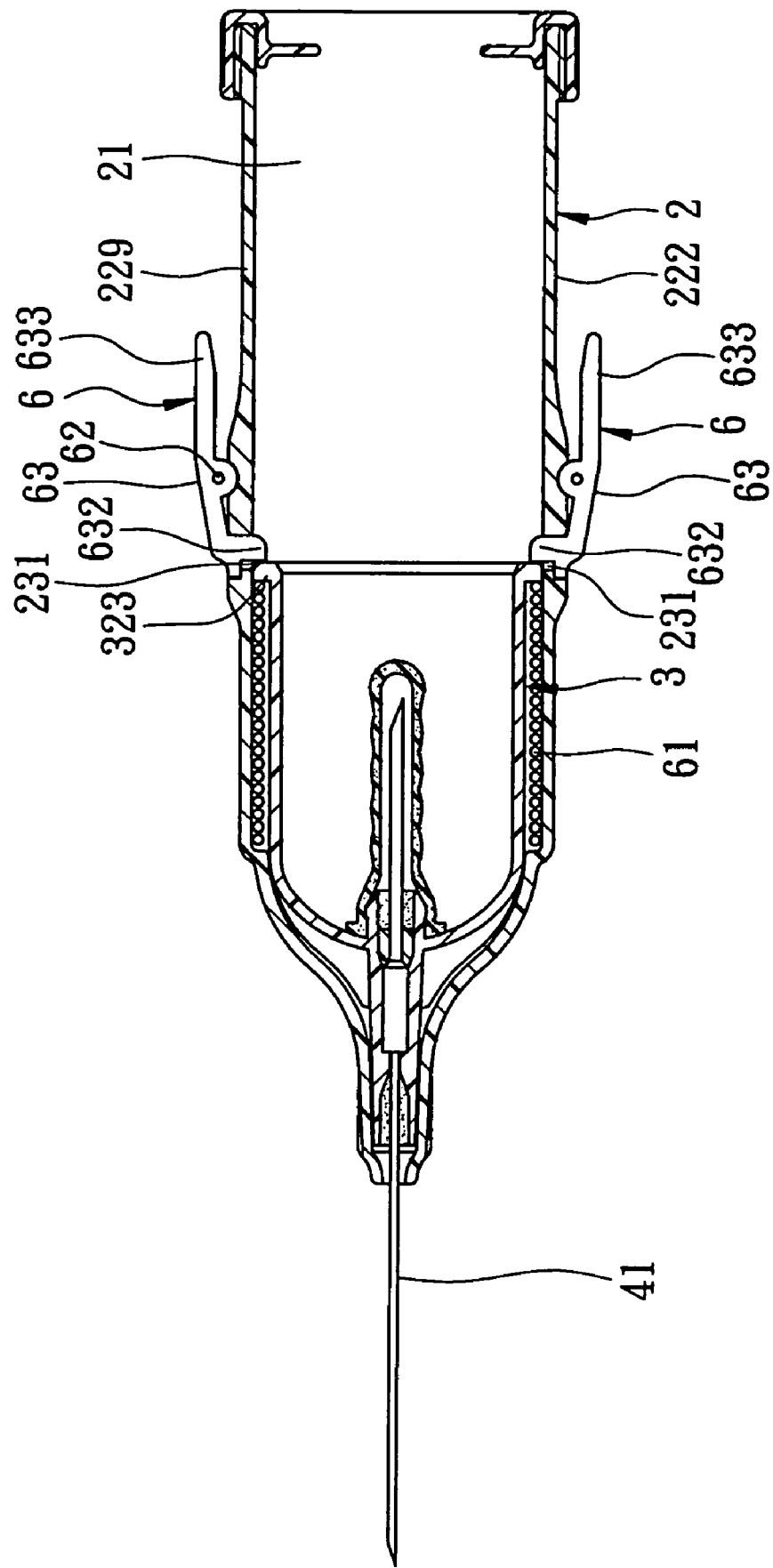
FIG. 13 is a sectional view of the third preferred embodiment wherein an additional triggering member is provided on the barrel.

Referring to FIG. 13, alternatively, the releasably retaining member may include two retaining holes 231 formed in the larger-diameter wall portion 229 for receiving two engaging pegs 632, and two triggering members 63 in the form of levers mounted pivotally on the outer barrel wall surface 222 by means of a C-shaped clip 62. The power ends 633 of the two triggering members 63 may be depressed symmetrically at the same time to perform a smooth retraction of the needle canula 41, thereby preventing shaking of the needle canula 41 during the retraction of the needle canula 41 to lessen the patient's pain.

Figure 14:
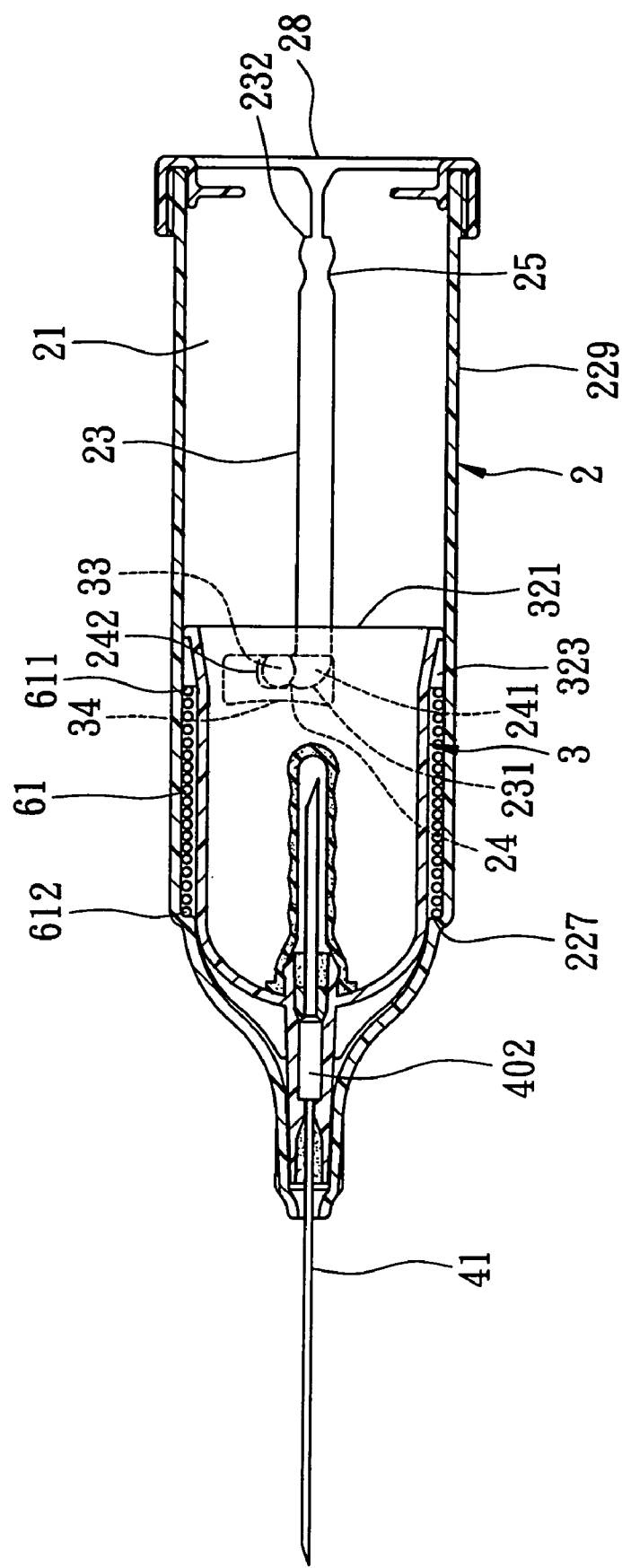
FIG. 14 is a sectional view of the fourth preferred embodiment of a cannula retractable medical collection device according to this invention.
Figure 15:
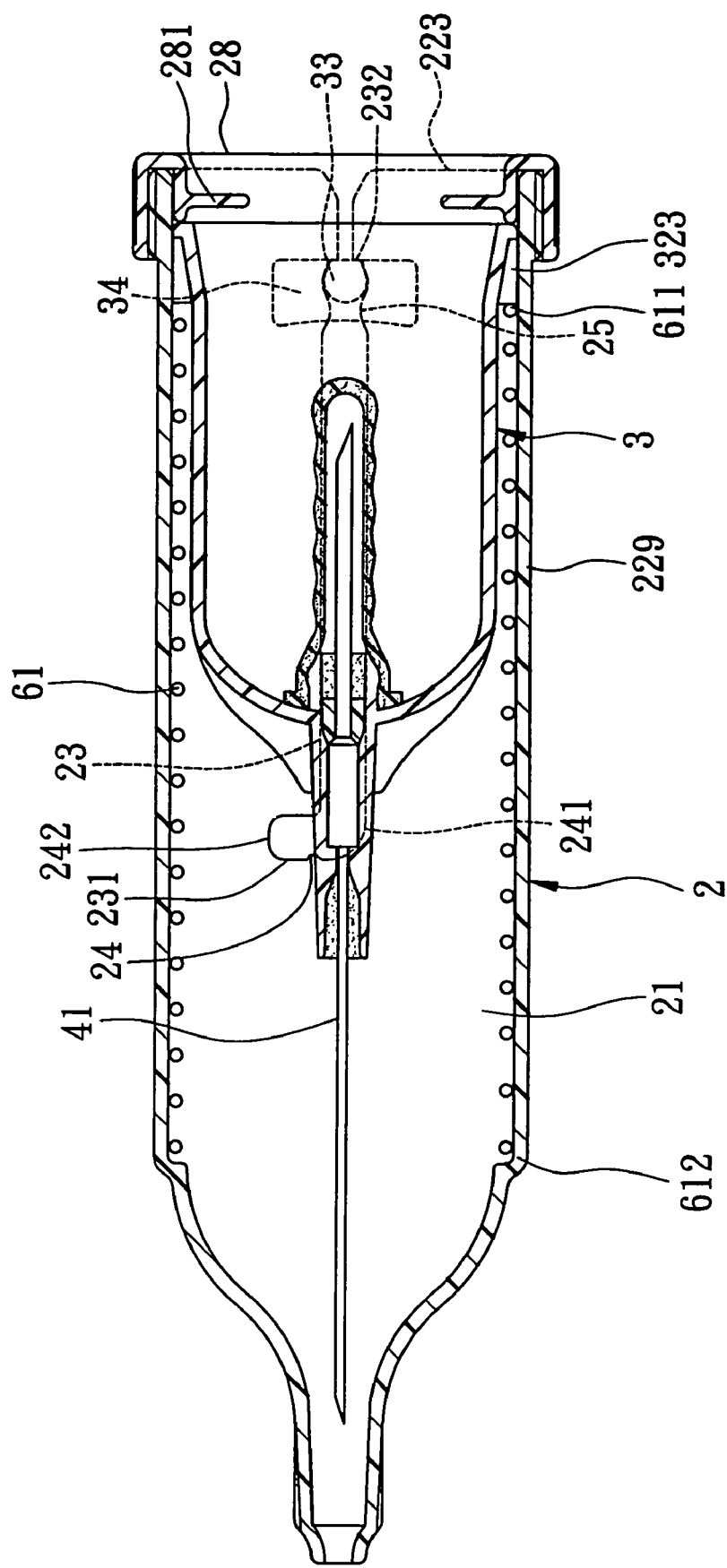
FIG. 15 is a sectional view of the fourth preferred embodiment, showing a needle cannula in a retracted state.

Referring to FIGS. 14 and 15, the fourth preferred embodiment of a cannula retractable medical collection device of this invention is shown to be similar to the second preferred embodiment in construction. In this embodiment, the retaining hole 231 includes a proximate connecting end 241 and a distal retaining end 242 which are opposite to each other in a transverse direction relative to the longitudinal direction, and which are proximate to and distal from the elongated guideway 23, respectively. A front constricted region 24 is formed between the proximate connecting end 241 and the distal retaining end 242. As such, the engaging peg 33 is engaged in the distal retaining end 242 to arrest the cannula mount 3 at the front position. Upon retraction of the needle cannula 41, the actuator 34 is operated to turn and move the engaging peg 33 from the distal retaining end 242 to the proximate connecting end 241 so as to permit rearward movement of the cannula mount 3 along the guideway 23. A coiled spring 61 is also provided to bias the cannula mount 3 to the rear position as illustrated in the third preferred embodiment.

Figure 16:
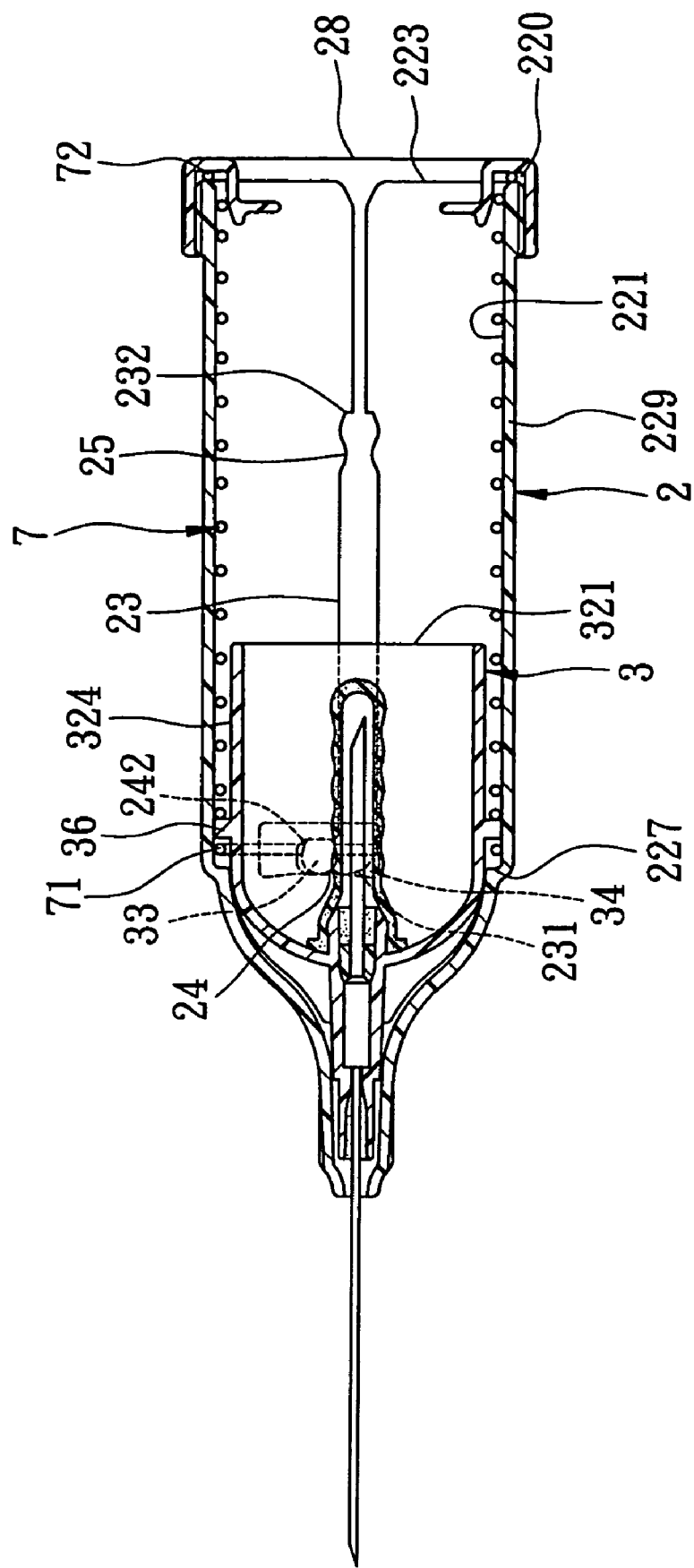
FIG. 16 is a sectional view of the fifth preferred embodiment of a cannula retractable medical collection device according to this invention.
Figure 17:
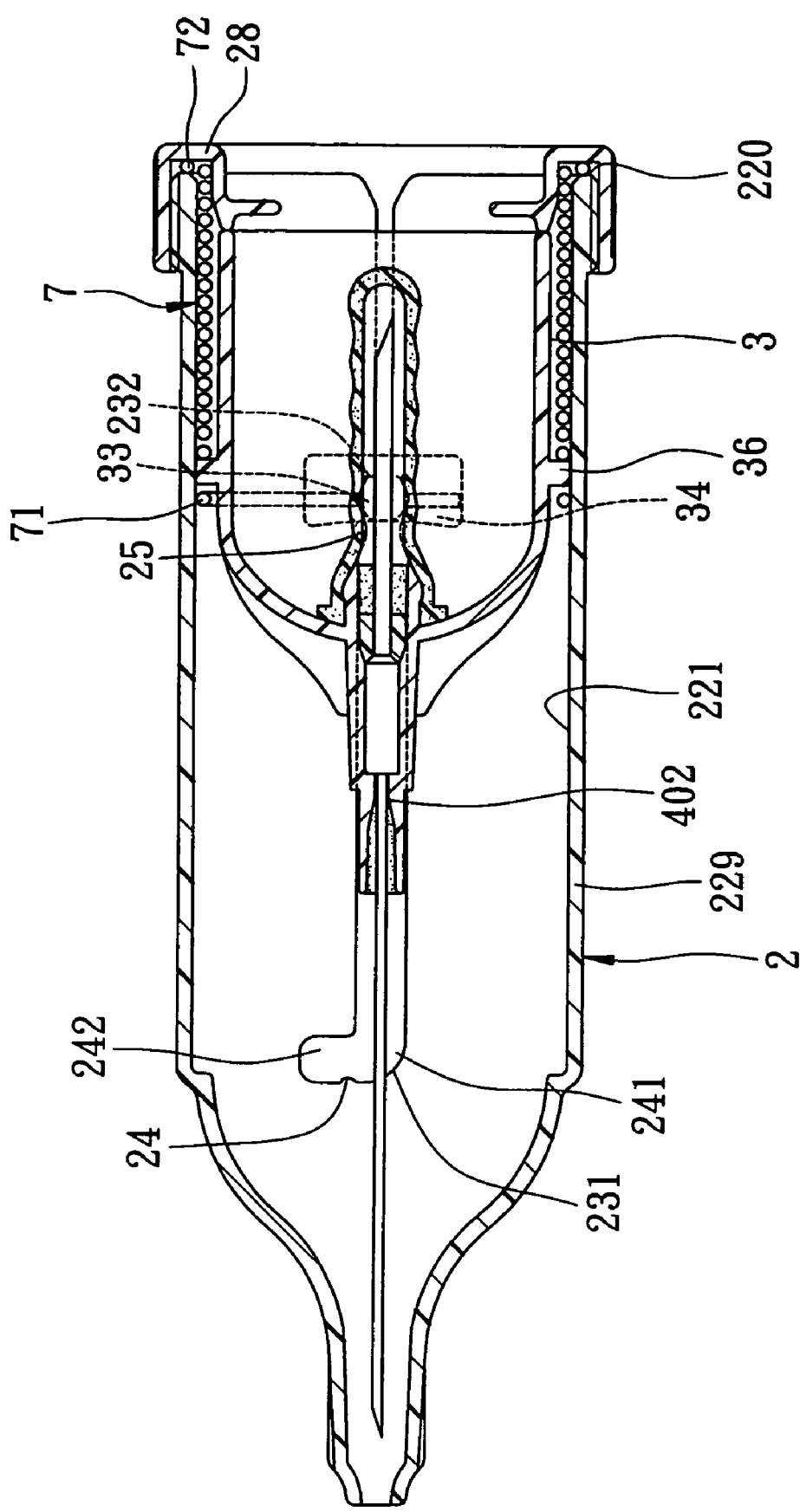
FIG. 17 is a sectional view of the fifth preferred embodiment, showing a needle cannula in a retracted state.

Referring to FIGS. 16 and 17, the fifth preferred embodiment of a cannula retractable medical collection device of this invention is shown to be similar to the fourth preferred embodiment in construction. The differences reside in that the skirt portion 324 of the cannula mount 3 and the inner barrel wall surface 221 of the larger-diameter wall portion 229 respectively have an annular flange 36 and an annular edge 220, which are opposite to and which confront each other in the longitudinal direction so as to define a biasing member receiving space therebetween and outside of the skirt portion 324. The coiled spring 7 is received in the biasing member receiving space, and has front and rear spring ends 71,72 secured to the flange 36 and the edge 220, respectively, such that the coiled spring 7 is tensioned by the cannula mount 3 when the cannula mount 3 is in the front position.

Figure 18:
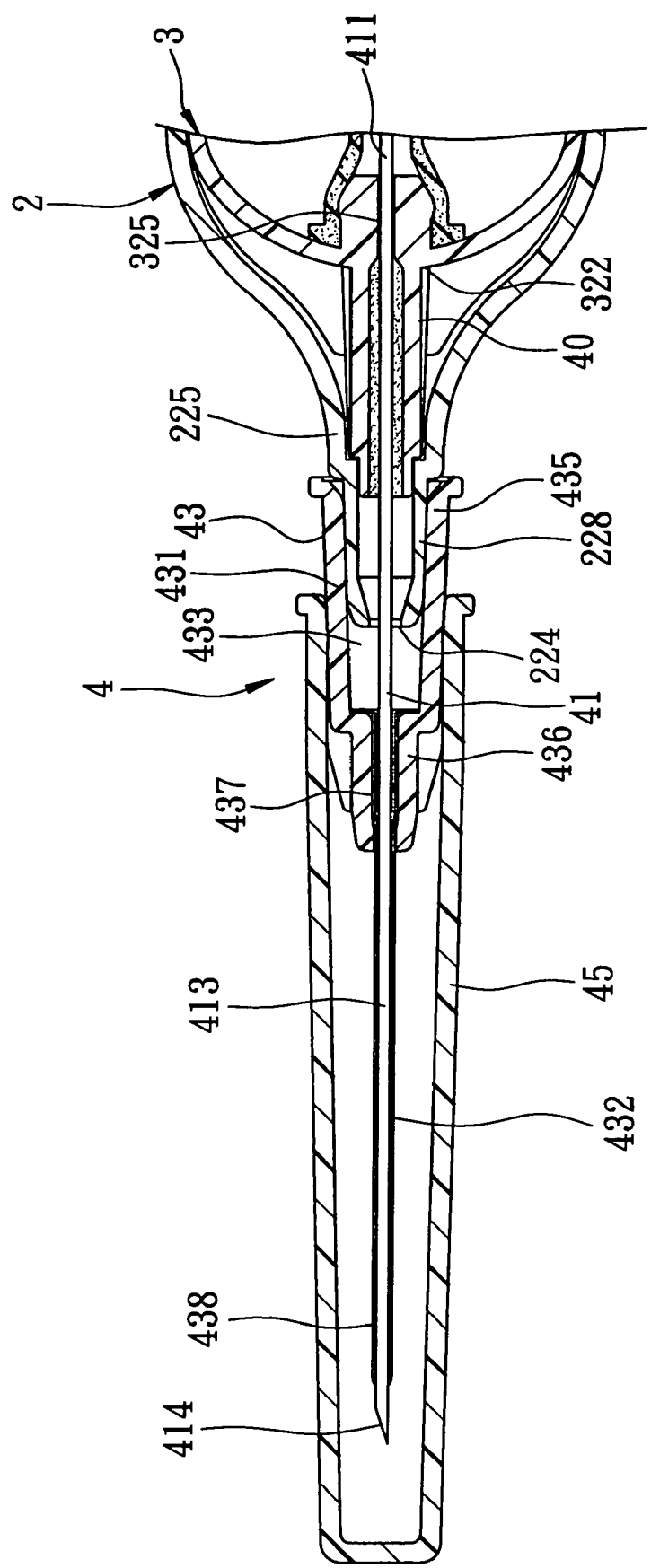
FIG. 18 is a fragmentary sectional view of the sixth preferred embodiment of a cannula retractable medical collection device according to this invention.
Figure 19:
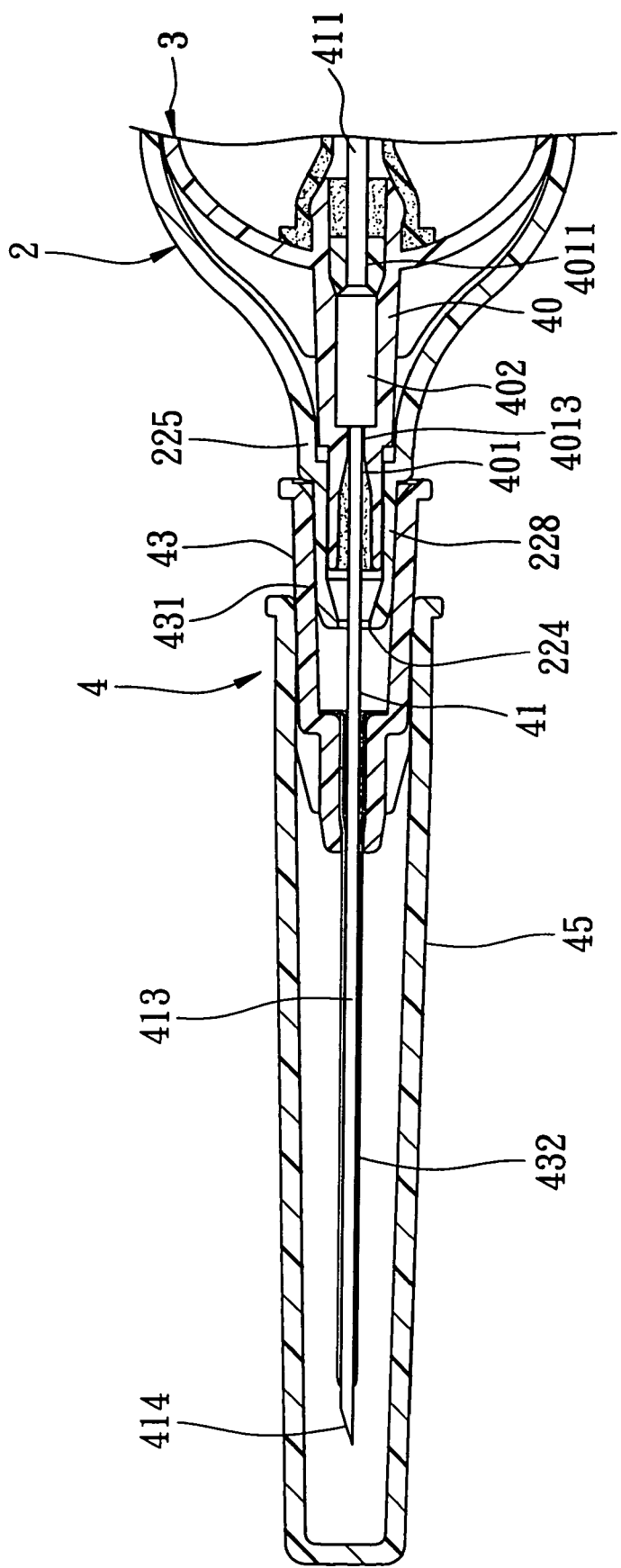
FIG. 19 is a fragmentary sectional view of the seventh preferred embodiment of a cannula retractable medical collection device according to this invention.

Referring to FIGS. 18 and 19, the sixth and seventh preferred embodiments of a cannula retractable medical collection device of this invention are shown to be similar to the previous embodiments in construction. In this embodiment, the needle assembly 4 further includes a detachable catheter device 43 including a catheter hub 431 and a tubular catheter 432. The catheter hub 431 defines a duct 433 therein, and includes a sleeve portion 435 which is detachably sleeved on a front sleeve region 228 of the smaller-diameter wall portion 225, and a tip portion 436 opposite to the sleeve portion 435 along the axis. The tubular catheter 432 has a proximate segment 437 which is disposed in the tip portion 436 and which extends along the axis to be communicated fluidly with the duct 433, and a distal segment 438 which extends from the proximate segment 437 along the axis to project outwardly of the tip portion 436. The front needle segment 413 of the needle cannula 41 extends through the tubular catheter 432 to have the front needle taper point 414 projecting outwardly of the distal segment 438 of the tubular catheter 432. Hence, when the front sleeve region 228 is removed from the catheter hub 431 with the removal of the needle cannula 41 from the catheter device 43 after completion of blood collection in the manner described above, the distal segment 438 of the tubular catheter 432 is left in the patient's vein for subsequent intravenous infusion process. In the seventh preferred embodiment shown in FIG. 19, the cannula holding passage 401, similar to that of the second preferred embodiment shown in FIG. 10, further has an enlarged light-transmissible intermediate portion 402 in the needle hub 40 to permit viewing of blood flowing therethrough.

Figure 20:
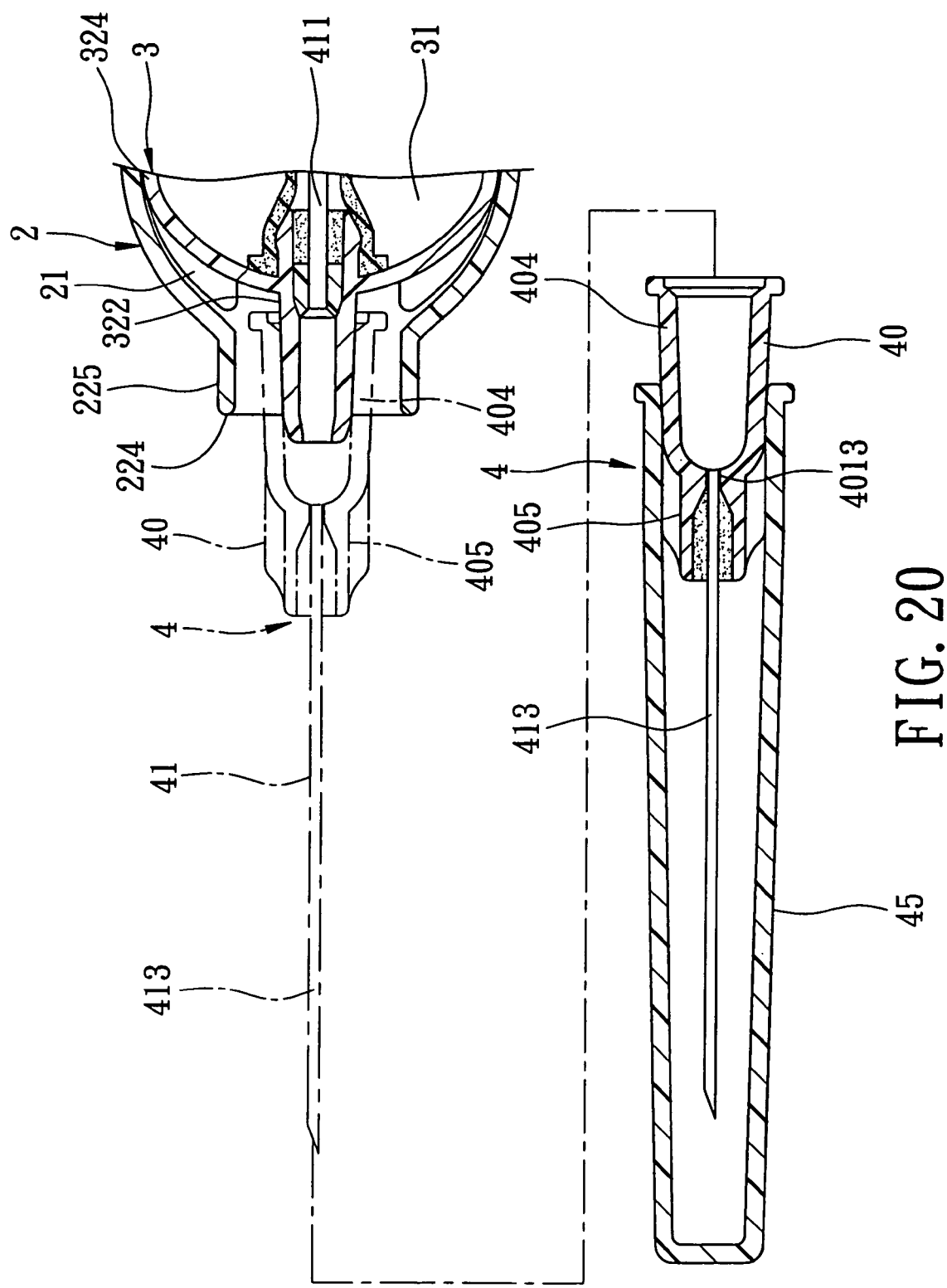
FIG. 20 is a fragmentary exploded sectional view of the eighth preferred embodiment of a cannula retractable medical collection device according to this invention.
Figure 21:
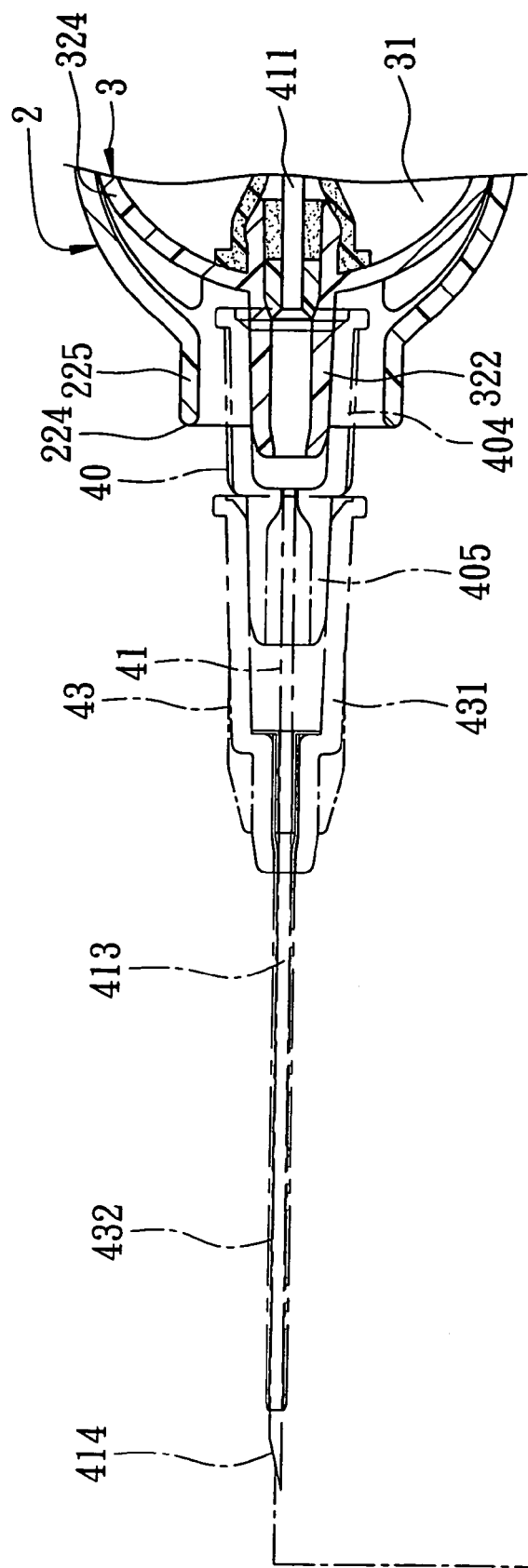
FIG. 21 is a fragmentary exploded sectional view of the ninth preferred embodiment of a cannula retractable medical collection device according to this invention.
Figure 21:
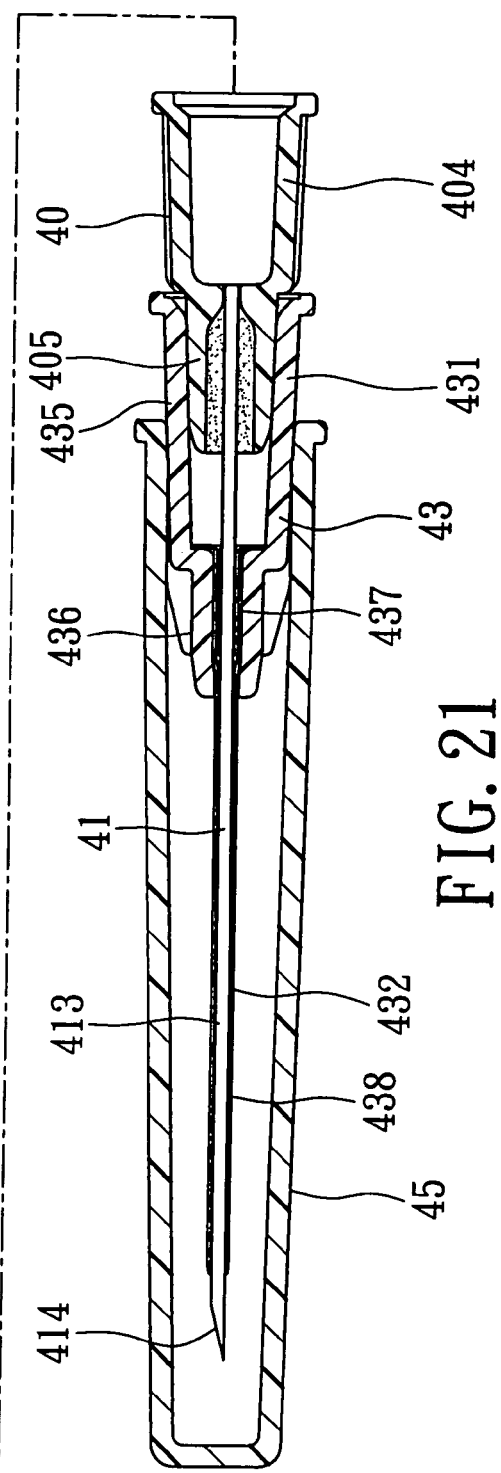

Referring to FIGS. 20 and 21, the eighth and ninth preferred embodiments of a canula retractable medical collection device of this invention are shown to be similar to the previous embodiments in construction. The differences reside in that the smaller-diameter wall portion 225 is formed to have an increased inner diameter of the front open end 224 such that a sleeve portion 404 of the needle hub 40 can be detachably sleeved on the interconnection portion 322 of the canula mount 3 through the front open end 224 along the axis. The sleeve portion 404 is light transmissible to permit viewing of blood flowing therethrough. The needle hub 40 further includes a holding portion 405 which is opposite to the sleeve portion 404 along the axis and which has a front passage segment 4013 for holding the front needle segment 413 of the needle canula 41. As such, the needle hub 40 can be used in conjunction with front needle segments 413 of different dimensions.

In the ninth preferred embodiment shown in FIG. 21, the needle assembly 4 further includes a detachable catheter device 43 including a catheter hub 431 and a tubular catheter 432 which are the same in construction as those of the sixth preferred embodiment in FIG. 18. The catheter hub 431 has a sleeve portion 435 sleeved on the holding portion 405 of the needle hub 40. Thus, the combination of a detachable catheter device 43 and a detachable needle hub 40 secured with the front needle segment 413 as a functional unit can be used as a detachable unit with different catheter dimensions for various clinical applications.

As illustrated, the cannula retractable medical collection device of this invention has the following advantages:

1. During operation, the user can hold the barrel 2 with one hand and operate the actuator 34,6 with a finger of the hand to cause the cannula mount 3 to move to the rear position so as to bring the front needle segment 413 into the disposal position. Therefore, the operation is convenient and safe to conduct.

2. Due to the provision of the deformable protrusions 282, the collection vial 5 can be held relative to the barrel 2 so that the collection vial 5 can be retained in the barrel 2 before insertion of the needle cannula 41 into the patient's vein, thereby facilitating operation of the collection device.

3. The cannula mount 3 is suitable for connection to the needle assembly 4 of various dimensions.

4. The catheter device 43 can be connected to the smaller-diameter wall portion 225 of the barrel 2 or the needle hub 40 such that the tubular catheter 432 is left in the patient's vein for intravenous injection immediately after completion of blood collection. In addition, the needle cannula 41 can be retracted after the barrel 2 and the needle assembly 4 are removed from the catheter device 43 with the holding hand. Therefore, the introduction of the tubular catheter 432 into the patient's vein is convenient and safe to conduct.

5. The enlarged intermediate portion 402 of the needle hub 40 is light transmissible to permit viewing of blood flowing therethrough so as to enable the user to check whether the needle cannula 41 has been properly inserted into the patient's vein.

While the present invention has been described in connection with what are considered the most practical and preferred embodiments, it is understood that this invention is not limited to the disclosed embodiments but is intended to cover various arrangements included within the spirit and scope of the broadest interpretations and equivalent arrangements.

We clam:

1. A cannula retractable medical collection device adapted to be used with a collection vial for collecting a blood sample therein, the collection vial having a front vial end and a pierceable stopper disposed on and covering the front vial end, said device comprising:

a barrel having front and rear open ends opposite to each other in a longitudinal direction, and a surrounding barrel wall which interconnects and which is interposed between said front and rear open ends, said surrounding barrel wall including a front smaller-diameter wall portion and a rear larger-diameter wall portion which are opposite to each other in the longitudinal direction and which are proximate to said front and rear open ends, respectively, said surrounding barrel wall having an inner barrel wall surface which surrounds an axis in the longitudinal direction and which confines a passage communicated with said front and rear open ends, and an outer barrel wall surface opposite to said inner barrel wall surface in radial directions relative to the axis;

a cannula mount inserted into said passage from said rear open end, and slidable relative to said rear larger-diameter wall portion along the axis between front and rear positions to be proximate to said smaller-diameter wall portion and said rear open end, respectively, said cannula mount including a shell member which has a skirt portion surrounding the axis and confining an accommodation chamber therein that is adapted for receiving the front vial end of the collection vial, and an interconnecting portion opposite to said skirt portion in the longitudinal direction, said interconnecting portion defining an axial passageway which extends therethrough to be communicated with said accommodation chamber;

a double-ended needle cannula including front and rear needle segments which are opposite to each other in the longitudinal direction, and which have front and rear needle taper points, respectively, said rear needle segment extending into said accommodation chamber through said axial passageway along the axis so as to enable said rear needle taper point to be adapted to prick the pierceable stopper when the front vial end of the collection vial is received in said accommodation chamber;

a needle hub disposed to secure said front needle segment to said interconnecting portion such that said front needle segment is in fluid communication with said rear needle segment, and such that when said cannula mount is in the front position, said front needle segment is placed in a position of use, where said front needle segment extends outwardly of said front open end for ready use, and when said cannula mount is in the rear position, said front needle segment is placed in a disposal position, where said front needle segment retreats inwardly and rearwardly of said front open end;

a releasably retaining member which is disposed to arrest axial movement of said cannula mount relative to said barrel when said cannula mount is in the front position, and which includes a retaining hole formed in said outer barrel wall surface of said larger-diameter wall portion, and extending in a radial direction through said inner barrel wall surface, and an engaging peg disposed to extend in the radial direction, and engageable in said retaining hole to establish an interengagement between said larger-diameter wall portion and said skirt portion such that movement of said cannula mount at the front position is arrested;

an actuator operable externally and disposed to enable said engaging peg to be disengaged from said retaining hole so as to permit the axial movement of said cannula mount to the rear position; and a plurality of deformable protrusions which are disposed on said inner barrel wall surface of said larger-diameter wall portion proximate to said rear open end and which extend radially and inwardly so as to be adapted to hold the collection vial by virtue of frictional engagement along the axis.

2. The cannula retractable medical collection device of claim 1, wherein said larger-diameter wall portion has an elongated guideway extending from said outer barrel wall surface through said inner barrel wall surface in the radial direction, and elongated from said retaining hole rearwardly and in the longitudinal direction to terminate at a rear retaining end, said engaging peg being disposed on and extending radially from said skirt portion to terminate at a shifted end which extends radially and outwardly of said outer barrel wall surface, and being slidable along said elongated guideway from said retaining hole to said rear retaining end when said cannula mount slides from the front position to the rear position.

3. The cannula retractable medical collection device of claim 2, wherein said actuator is formed integrally with said shifted end of said engaging peg, and is disposed outwardly of and is slidable relative to said outer barrel wall surface.

4. The cannula retractable medical collection device of claim 3, wherein said elongated guideway has front and rear constricted regions which are formed immediately behind said retaining hole and immediately in front of said rear retaining end, respectively, such that once said engaging peg is forced through one of said front and rear constricted regions, movement of said engaging peg is arrested by virtue of a snap-fit in a corresponding one of said retaining hole and said rear retaining end so as to place said cannula mount in a corresponding one of the front and rear positions.

5. The cannula retractable medical collection device of claim 4, wherein said larger-diameter wall portion further has a split which extends from said rear retaining end of said elongated guideway to said rear open end.

6. The cannula retractable medical collection device of claim 3, wherein said retaining hole includes a proximate connecting end and a distal retaining end which are opposite to each other in a transverse direction relative to the longitudinal direction and which are proximate to and distal from said elongated guideway, respectively, such that said engaging peg is engaged in said distal retaining end to arrest movement of said cannula mount at the front position, and such that said actuator is operated to move said engaging peg from said distal retaining end to said proximate connecting end so as to permit slidable movement of said engaging peg along said elongated guideway.

7. The cannula retractable medical collection device of claim 6, further comprising a biasing member which is interposed between said skirt portion and said inner barrel wall surface, and which is disposed to bias said cannula mount toward the rear position.

8. The cannula retractable medical collection device of claim 7, wherein said inner barrel wall surface of said larger-diameter wall portion and said skirt portion respectively have an annular shoulder and a flange which are opposite to and which confront each other in the longitudinal direction so as to define a biasing member receiving space therebetween, said biasing member being a coiled spring which has front and rear spring ends abutting against said annular shoulder and said flange, respectively, such that said coiled spring is compressed by said cannula mount when said cannula mount is in the front position.

9. The cannula retractable medical collection device of claim 7, wherein said skirt portion and said inner barrel wall surface of said larger-diameter wall portion respectively have an annular flange and an edge which are opposite to and which confront each other in the longitudinal direction so as to define a biasing member receiving space therebetween, said biasing member being a coiled spring which has front and rear spring ends secured to said annular flange and said edge, respectively, such that said coiled spring is tensioned by said cannula mount when said cannula mount is in the front position.

10. The cannula retractable medical collection device of claim 1, wherein said actuator includes a triggering member which is pivotally mounted on said outer barrel wall surface at a fulcrum point, and which includes a weight end formed integrally with said engaging peg, and a power end disposed at an opposite side of said weight end relative to said fulcrum point so as to be actuated to move said engaging peg in the radial direction to withdraw from said passage, said device further comprising a biasing member which is disposed between said skirt portion and said inner barrel wall surface to bias said cannula mount toward the rear position.

11. The cannula retractable medical collection device of claim 1, wherein said front and rear needle segments are formed integrally with each other.

12. The cannula retractable medical collection device of claim 1, wherein said needle hub has a cannula holding passage extending along the axis and fluidly communicated with said axial passageway, said cannula holding passage including front and rear passage segments for receiving said front and rear needle segments, respectively, and an intermediate portion interconnecting said front and rear passage segments and being light transmissible to permit viewing of blood flowing therethrough.

13. The cannula retractable medical collection device of claim 1, further comprising:

a catheter hub defining a duct therein, and including a sleeve portion which is detachably sleeved on said smaller-diameter wall portion, and a tip portion opposite to said sleeve portion along the axis; and a tubular catheter having a proximate segment which is disposed in said tip portion and which extends along the axis to be communicated fluidly with said duct, and a distal segment which extends from said proximate segment along the axis to project outwardly of said tip portion, said front needle segment of said needle cannula extending through said tubular catheter to have said front needle taper point projecting outwardly of said distal segment of said tubular catheter.

14. The cannula retractable medical collection device of claim 1, wherein said needle hub includes a sleeve portion which is detachably sleeved on said interconnecting portion from said front open end of said barrel along the axis, and which is light transmissible to permit viewing of blood flowing therethrough, and a holding portion which is opposite to said sleeve portion along the axis and which is disposed to hold said front needle segment of said needle cannula.

15. The cannula retractable medical collection device of claim 14, further comprising:

a catheter hub defining a duct therein, and including a sleeve portion which is detachably sleeved on said holding portion of said needle hub, and a tip portion opposite to said sleeve portion along the axis; and a tubular catheter having a proximate segment which is disposed in said tip portion and which extends along the axis to be communicated fluidly with said duct, and a distal segment which extends from said proximate segment along the axis to project outwardly of said tip portion, said front needle segment of said needle cannula extending through said tubular catheter to have said front needle taper point projecting outwardly of said distal segment of said tubular catheter.

16. The cannula retractable medical collection device of claim 1, wherein said cannula mount is formed integrally with said needle hub, said inner barrel wall surface of said smaller-diameter wall portion being converged gradually from said larger-diameter wall portion towards said front open end.

* * * * *